US007527935B2

(12) United States Patent
Onuki et al.

(10) Patent No.: US 7,527,935 B2
(45) Date of Patent: May 5, 2009

(54) G-PROTEIN COUPLED RECEPTOR HAVING EICOSANOID AS LIGAND AND GENE THEREOF

(75) Inventors: Tetsuo Onuki, Saitama (JP); Yutaka Koguchi, Exton, PA (US); Emiko Hosoi, Saitama (JP); Aiko Chikada, Saitama (JP); Takeshi Hosoi, Saitama (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 0 days.

(21) Appl. No.: 10/943,848

(22) Filed: Sep. 20, 2004

(65) Prior Publication Data

US 2005/0106603 A1 May 19, 2005

Related U.S. Application Data

(63) Continuation-in-part of application No. PCT/JP03/03042, filed on Mar. 14, 2003.

(60) Provisional application No. 60/517,919, filed on Nov. 7, 2003.

(30) Foreign Application Priority Data

Mar. 19, 2002 (JP) ............................. 2002-075724

(51) Int. Cl.
*G01N 33/566* (2006.01)
*C07K 14/705* (2006.01)
(52) U.S. Cl. .................... 435/7.21; 435/7.2; 436/501
(58) Field of Classification Search ................ None
See application file for complete search history.

(56) References Cited

U.S. PATENT DOCUMENTS 5,955,308 A * 9/1999 Bergsma et al. ............ 435/69.1

FOREIGN PATENT DOCUMENTS

| DE | 100 21 475 A1 | 11/2001 |
|---|---|---|
| EP | 0 892 051 A2 | 1/1999 |
| WO | WO 00/28032 A2 | 5/2000 |
| WO | WO 00/71584 A1 | 11/2000 |
| WO | WO 01/31014 A2 | 5/2001 |
| WO | WO 01/36471 A2 | 5/2001 |
| WO | WO 01/57182 | 8/2001 |
| WO | WO 01/85791 A1 | 11/2001 |
| WO | WO 01/94385 A2 | 12/2001 |
| WO | WO 02/00719 A2 | 1/2002 |

OTHER PUBLICATIONS

O'Flaherty et al. The Coupling of 5OOxo-Eicosanoid Receptors to Heterotrimeric G Proteins. Mar. 15, 2000, J. Immunol. 164(6):3345-3352.*
O'Flaherty et al. Receptors for the 5-Oxo Class of Eicosanoids in Neutrophils. Dec. 4, 1998, J. Biol. Chem. 273(49):32535-32541.*
Boie, Yves et al., "Molecular Cloning and Characterization of the Human Prostanoid DP Receptor", Journal of Biological Chemistry; vol. 270, No. 32, Aug. 11, 1995, pp. 18910-18916.
Funk, Colin D. et al, "Cloning and Expression of a cDNA for the Human Prostaglandin E Receptor EP, Subtype", Journal of Biological Chemistry, vol. 268, No. 35, Dec. 15, 1993, pp. 26767-26772.
Hosoi, Takeshi et al., "Identification of a Novel Human Eicosanoid Receptor Coupled to $G_{i/o}$", Journal of Biological Chemistry, vol. 277, No. 35, Aug. 30, 2002, pp. 31459-31465.
Takeda, Shigeki et al., "Identification of a G-Protein-Coupled Receptor for 5-oxo-Eicosatetraenoic Acid", Biomedical Research, vol. 23, No. 2, 2002, pp. 101-108.
Takeda, Shigeki et al., "Identification of G protein-coupled receptor genes from the human genome sequence", FEBS Letters, vol. 520, 2002, pp. 97-101.
"*Homo sapiens* chromosome 2 clone RP11-489G24 map 2", Accession No. AC013396, Mar. 16, 2000.
"*Homo sapiens* GPCR gene for putative G-protein coupled receptor, complete CDS, clone:hGPCR48", Accession No. AB083630, May 24, 2002.
"*Homo sapiens* tg 1019 mRNA fri G-protein coupled receptor, complete cds", Accession No. AB083055, Sep. 6, 2002.
Avis, Ingalill et al., "Five-lipoxygenase Inhibitors can Mediate Apoptosis in Human Breast Cancer Cell Lines through Complex Eicosanoid Interactions", *The FASEB Journal*, vol. 15, pp. 2007-2009, Sep. 2001.
Avis, Ingalill et al., "Growth Control of Lung Cancer by Interruption of 5-Lipoxygenase-mediated Growth Factor Signaling", *Journal of Clinical Investigation*, vol. 97, No. 3, pp. 806-813, Feb. 1996.
Ding, Xian-Zhong et al. "Lipoxygenase Inhibitors Abolish Proliferation of Human Pancreatic Cancer Cells", *Biochemical and Biophysical Research Communications*, vol. 261, pp. 218-223, 1999.
Ghosh, Jagadananda et al., "Arachidonic Acid Stimulates Prostate Cancer Cell Growth: Critical Role of 5-Lipoxygenase", *Biochemical and Biophysical Research*, vol. 235, pp. 418-423, 1997.
Ghosh, Jagadananda et al., "Inhibition of Arachidonate 5-lipoxygenase Triggers Massive Apoptosis in Human Prostate Cancer Cells", *Proceedings of the National Academy Sciences of the Unites States of America*, vol. 95, pp. 13182-13187, Oct. 1998.

(Continued)

*Primary Examiner*—John D Ulm
(74) *Attorney, Agent, or Firm*—Browdy and Neimark P.L.L.C.

(57) ABSTRACT

The present invention provides a polypeptide selected from the following (A), (B) and (C), having a function or an activity as a receptor of an eicosanoid (5-oxo-ETE, etc.);
 (A) a polypeptide comprising an amino acid sequence shown by SEQ ID NO:2 or SEQ ID NO:21;
 (B) a polypeptide comprising an amino acid sequence shown by SEQ ID NO: 2 or SEQ.ID.NO:21 in which one or several amino acids are deleted, substituted or added;
 (C) a polypeptide encoded by a nucleic acid which hybridizes under stringent condition with a nucleic acid comprising a nucleotide sequence shown by SEQ ID NO:1 or SEQ ID NO:20 or a complement thereof,
a nucleic acid encoding the polypeptide, a recombinant vector and a host cell comprising the same, a method for detecting a function or an activity of the polypeptide using the same, and a method for screening or identifying a ligand or an effector (an agonist or an antagonist) of the polypeptide using the same, a pharmaceutical composition comprising an antagonist of the polypeptide, and a therapeutic method using the antagonist, etc.

7 Claims, 10 Drawing Sheets

OTHER PUBLICATIONS

Guilbert, Martin et al., "5-Oxo-6,8,11,14-Eicosatetraenoic Acid Induces Important Eosinophil Transmigration through Basement Membrane Components Comparison of Normal and Asthmatic Eosinophils", *American Journal of Respiratory Cell and Molecular Biology*, vol. 21, pp. 97-104, 1999.

Mohammed Akbar, G. K. et al., "Molecular Cloning of a Novel P2 Purinoceptor from Human Erythroleukemia Cells", *Journal of Biological Chemistry*, vol. 271, No. 31, pp. 18363-18367, Aug. 1996.

Narumiya, Shuh et al., "Prostanoid Receptors: Structures, Properties, and Functions", *Physiological Reviews*, vol. 70, No. 4, pp. 1193-1226, Oct. 1999.

Romano, Mario et al., "5-Lipoxygenase Regulates Malignant Mesothelial Cell Survival: Involvement of Vascular Endothelial Growth Factor", *The FASEB Journal*, vol. 15, pp. 2326-2336, Nov. 2001.

Schwenk; Uwe et al., "5-Oxo-eicosanoids are Potent Eosinophil Chemotactic Factors", *Journal of Biological Chemistry*, vol. 270, No. 25, pp. 15029-15036, Jun. 1995.

Stamatiou, Panaglota et al., "5-Oxo-ETE Induces Pulmonary Eosinophilia in an Integrin-Dependent Manner in Brown Norway Rats", *Journal of Clinical Investigation*, vol. 102, No. 12, pp. 2165-2172, Dec. 1998.

\* cited by examiner

Fig. 2

```
                                           Me tLeuCysHis ArgGlyGlyG
  1  TTCTCAGTGG CTGCGAGAAT GCTGATGAAA ACCCCAGGAT GTTGTGTCAC CGTGGTGGCC lnLeuIleVa lProIleIle ProLeuCysP roGluHisSe rCysArgGly ArgArgLeuG
 61  AGCTGATAGT GCCAATCATC CCACTTTGCC CTGAGCACTC CTGCAGGGGT AGAAGACTCC lnAsnLeuLe uSerGlyPro TrpProLysG lnProMetGl uLeuHisAsn LeuSerSerP
121  AGAACCTTCT CTCAGGCCCA TGGCCCAAGC AGCCCATGGA ACTTCATAAC CTGAGCTCTC roSerProSe rLeuSerSer SerValLeuP roProSerPh eSerProSer ProSerSerA
181  CATCTCCCTC TCTCTCCTCC TCTGTTCTCC CTCCCTCCTT CTCTCCCTCA CCCTCCTCTG laProSerAl aPheThrThr ValGlyGlyS erSerGlyGl yProCysHis ProThrSerS
241  CTCCCTCTGC CTTTACCACT GTGGGGGGGT CCTCTGGAGG GCCCTGCCAC CCCACCTCTT erSerLeuVa lSerAlaPhe LeuAlaProI leLeuAlaLe uGluPheVal LeuGlyLeuV
301  CCTCGCTGGT GTCTGCCTTC CTGGCACCAA TCCTGGCCCT GGAGTTTGTC CTGGGCCTGG alGlyAsnSe rLeuAlaLeu PheIlePheC ysIleHisTh rArgProTrp ThrSerAsnT
361  TGGGGAACAG TTTGGCCCTC TTCATCTTCT GCATCCACAC GCGGCCCTGG ACCTCCAACA hrValPheLe uValSerLeu ValAlaAlaA spPheLeuLe uIleSerAsn LeuProLeuA
421  CGGTGTTCCT GGTCAGCCTG GTGGCCGCTG ACTTCCTCCT GATCAGCAAC CTGCCCCTCC rgValGlyTy rTyrLeuLeu HisGluThrT rpArgPheGl yAlaAlaAla CysLysValA
481  GCGTGGGCTA CTACCTCCTC CATGAGACCT GGCGCTTTGG GGCTGCTGCC TGCAAAGTCA snLeuPheMe tLeuSerThr AsnArgThrA laSerValVa lPheLeuThr AlaIleAlaL
541  ACCTCTTCAT GCTGTCCACC AACCGCACGG CCAGCGTTGT CTTCCTCACA GCCATCGCAC euAsnArgTy rLeuLysVal ValGlnProH isHisValLe uSerArgAla SerValGlyA
601  TCAACCGCTA CCTGAAGGTG GTGCAGCCCC ACCACGTGCT GAGCCGTGCT TCCGTGGGGG laAlaAlaAr gValAlaGly GlyLeuTrpV alGlyIleLe uLeuLeuAsn GlyHisLeuL
661  CAGCTGCCCG GGTGGCCGGG GGACTCTGGG TGGGCATCCT GCTCCTCAAC GGGCACCTGC euLeuSerTh rPheSerGly ProSerCysL euSerTyrAr gValGlyThr GluProSerA
721  TCCTGAGCAC CTTCTCCGGC CCCTCCTGCC TCAGCTACAG GGTGGGCACG GAGCCCTCGG laSerLeuAr gTrpHisGln AlaLeuTyrL euLeuGluPh ePheLeuPro LeuAlaLeuI
781  CCTCGCTCCG CTGGCACCAG GCACTGTACC TGCTGGAGTT CTTCCTGCCA CTGGCGCTCA leLeuPheAl aIleValSer IleGlyLeuT hrIleArgAs nArgGlyLeu GlyGlyGlnA
841  TCCTCTTTGC TATTGTGAGC ATTGGGCTCA CCATCCGGAA CCGTGGTCTG GGCGGGCAGG laGlyProGl nArgAlaMet ArgValLeuA laMetValVa lAlaValTyr ThrIleCysP
901  CAGGCCCGCA GAGGGCCATG CGTGTGCTGG CCATGGTGGT GGCCGTCTAC ACCATCTGCT heLeuProSe rIleIlePhe GlyMetAlaS erMetValAl aPheTrpLeu SerAlaCysA
961  TCTTGCCCAG CATCATCTTT GGCATGGCTT CCATGGTGGC TTTCTGGCTG TCCGCCTGCC rgSerLeuAs pLeuCysAla GlnLeuPheH isGlySerLe uAlaPheThr TyrLeuAsnS
1021 GCTCCCTGGA CCTCTGCGCA CAGCTCTTCC ATGGCTCCCT GGCCTTCACC TACCTCAACA erValLeuAs pProValLeu TyrCysPheS erSerProAs nPheLeuHis GlnSerArgA
1081 GTGTCCTGGA CCCCGTGCTC TACTGCTTCT CTAGCCCCAA CTTCCTCCAC CAGAGCCGGG laLeuLeuGl yLeuThrArg GlyArgGlnG lyProValSe rAspGluSer SerTyrGlnP
1141 CCTTGCTGGG CCTCACGCGG GGCCGGCAGG GCCCAGTGAG CGACGAGAGC TCCTACCAAC roSerArgGl nTrpArgTyr ArgGluAlaS erArgLysAl aGluAlaIle GlyLysLeuL
1201 CCTCCAGGCA GTGGCGCTAC CGGGAGGCCT CTAGGAAGGC GGAGGCCATA GGGAAGCTGA ysValGlnGl yGluValSer LeuGluLysG luGlySerSe rGlnGly***
1261 AAGTGCAGGG CGAGGTCTCT CTGGAAAAGG AAGGCTCCTC CCAGGGCTGA GGGCCAGCTG

1321 CAGGGCTGCA GCGCTGTGGG GGTAAGGGCT GCCGCGCTCT GGCCTGGAGG GACAAGGCCA

1381 GCACACGGTG CCTCAACCAA CTGGACAAGG GATGGCGGCA GACCAGGGGC CAGGCCAAAG

1441 CATGGCAGGG ACTCAGGTGG GT
```

Fig. 3

| | | | | | | | | | | |
|---|---|---|---|---|---|---|---|---|---|---|
| Total Brain | Cerebellum (Left) | Substantia Nigra | Heart | Esophagus | Transverse Colon | Kidney | Lung | Liver | Leukemia Cell HL-60 | Fetal Brain |
| Cerebral Cortex | Cerebellum (Right) | Accumbens Nucleus | Aorta | Stomach | Descending Colon | Skeletal Muscle | Placenta | Pancreas | HeLa Cell S3 | Fetal Heart |
| Frontal Lobe | Corpus Callosum | Thalamus | Left Atrium | Duodenum | Rectum | Spleen | Bladder | Adrenal Gland | Leukemia Cell K-562 | Fetal Kidney |
| Parietal Lobe | Amygdala | Pituitary Gland | Right Atrium | Jejunum | | Thymus | Uterus | Thyroid Gland | Leukemia Cell MOLT-4 | Fetal Liver |
| Occipital Lobe | Caudate Nucleus | Spinal Cord | Left Ventricle | Ileum | | Peripheral Blood Leukocyte | Prostate | Salivary Gland | Burkittt Lymphoma Cell Raji | Fetal Spleen |
| Temporal Lobe | Hippocampus | | Right Ventricle | Ileocecum | | Lymph Node | Testis | Mammary Gland | Burkitt Lymphoma Cell Daudi | Fetal Thymus |
| Cerebral Cortex Paracentral Gyrus | Medulla Oblongata | | Interventricular Septum | Appendix Vermiformis | | Bone Marrow | Ovary | | Colorectal Adenocarcinoma Cell Sw480 | Fetal Lung |
| Pons | Putamen | | Apex of the Heart | Ascending Colon | | Trachea | | | Lung Carcinoma Cell A549 | |

SEQUENCE LISTING

```
<160> NUMBER OF SEQ ID NOS: 23

<210> SEQ ID NO 1
<211> LENGTH: 1462
<212> TYPE: DNA
<213> ORGANISM: Homo sapiens
<220> FEATURE:
<221> NAME/KEY: CDS
<222> LOCATION: (39)..(1307)
<223> OTHER INFORMATION:

<400> SEQUENCE: 1
ttctcagtgg ctgcgagaat gctgatgaaa accccagg atg ttg tgt cac cgt ggt      56
                                          Met Leu Cys His Arg Gly
                                          1               5 ggc cag ctg ata gtg cca atc atc cca ctt tgc cct gag cac tcc tgc     104
Gly Gln Leu Ile Val Pro Ile Ile Pro Leu Cys Pro Glu His Ser Cys
         10                  15                  20 agg ggt aga aga ctc cag aac ctt ctc tca ggc cca tgg ccc aag cag     152
Arg Gly Arg Arg Leu Gln Asn Leu Leu Ser Gly Pro Trp Pro Lys Gln
     25                  30                  35 ccc atg gaa ctt cat aac ctg agc tct cca tct ccc tct ctc tcc tcc     200
Pro Met Glu Leu His Asn Leu Ser Ser Pro Ser Pro Ser Leu Ser Ser
```

```
            40                  45                  50
tct gtt ctc cct ccc tcc ttc tct ccc tca ccc tcc tct gct ccc tct        248
Ser Val Leu Pro Pro Ser Phe Ser Pro Ser Pro Ser Ser Ala Pro Ser
 55                  60                  65                  70 gcc ttt acc act gtg ggg ggg tcc tct gga ggg ccc tgc cac ccc acc        296
Ala Phe Thr Thr Val Gly Gly Ser Ser Gly Gly Pro Cys His Pro Thr
                 75                  80                  85 tct tcc tcg ctg gtg tct gcc ttc ctg gca cca atc ctg gcc ctg gag        344
Ser Ser Ser Leu Val Ser Ala Phe Leu Ala Pro Ile Leu Ala Leu Glu
                 90                  95                 100 ttt gtc ctg ggc ctg gtg ggg aac agt ttg gcc ctc ttc atc ttc tgc        392
Phe Val Leu Gly Leu Val Gly Asn Ser Leu Ala Leu Phe Ile Phe Cys
                105                 110                 115 atc cac acg cgg ccc tgg acc tcc aac acg gtg ttc ctg gtc agc ctg        440
Ile His Thr Arg Pro Trp Thr Ser Asn Thr Val Phe Leu Val Ser Leu
        120                 125                 130 gtg gcc gct gac ttc ctc ctg atc agc aac ctg ccc ctc cgc gtg ggc        488
Val Ala Ala Asp Phe Leu Leu Ile Ser Asn Leu Pro Leu Arg Val Gly
135                 140                 145                 150 tac tac ctc ctc cat gag acc tgg cgc ttt ggg gct gct gcc tgc aaa        536
Tyr Tyr Leu Leu His Glu Thr Trp Arg Phe Gly Ala Ala Ala Cys Lys
                155                 160                 165 gtc aac ctc ttc atg ctg tcc acc aac cgc acg gcc agc gtt gtc ttc        584
Val Asn Leu Phe Met Leu Ser Thr Asn Arg Thr Ala Ser Val Val Phe
                170                 175                 180 ctc aca gcc atc gca ctc aac cgc tac ctg aag gtg gtg cag ccc cac        632
Leu Thr Ala Ile Ala Leu Asn Arg Tyr Leu Lys Val Val Gln Pro His
        185                 190                 195 cac gtg ctg agc cgt gct tcc gtg ggg gca gct gcc cgg gtg gcc ggg        680
His Val Leu Ser Arg Ala Ser Val Gly Ala Ala Ala Arg Val Ala Gly
200                 205                 210 gga ctc tgg gtg ggc atc ctc ctc aac ggg cac ctg ctc ctg agc        728
Gly Leu Trp Val Gly Ile Leu Leu Asn Gly His Leu Leu Leu Ser
215                 220                 225                 230 acc ttc tcc ggc ccc tcc tgc ctc agc tac agg gtg ggc acg gag ccc        776
Thr Phe Ser Gly Pro Ser Cys Leu Ser Tyr Arg Val Gly Thr Glu Pro
                235                 240                 245 tcg gcc tcg ctc cgc tgg cac cag gca ctg tac ctg ctg gag ttc ttc        824
Ser Ala Ser Leu Arg Trp His Gln Ala Leu Tyr Leu Leu Glu Phe Phe
        250                 255                 260 ctg cca ctg gcg ctc atc ctc ttt gct att gtg agc att ggg ctc acc        872
Leu Pro Leu Ala Leu Ile Leu Phe Ala Ile Val Ser Ile Gly Leu Thr
        265                 270                 275 atc cgg aac cgt ggt ctg ggc ggg cag gca ggc ccg cag agg gcc atg        920
Ile Arg Asn Arg Gly Leu Gly Gly Gln Ala Gly Pro Gln Arg Ala Met
280                 285                 290 cgt gtg ctg gcc atg gtg gtg gcc gtc tac acc atc tgc ttc ttg ccc        968
Arg Val Leu Ala Met Val Val Ala Val Tyr Thr Ile Cys Phe Leu Pro
295                 300                 305                 310 agc atc atc ttt ggc atg gct tcc atg gtg gct ttc tgg ctg tcc gcc       1016
Ser Ile Ile Phe Gly Met Ala Ser Met Val Ala Phe Trp Leu Ser Ala
                315                 320                 325 tgc cgc tcc ctg gac ctc tgc gca cag ctc ttc cat ggc tcc ctg gcc       1064
Cys Arg Ser Leu Asp Leu Cys Ala Gln Leu Phe His Gly Ser Leu Ala
                330                 335                 340 ttc acc tac ctc aac agt gtc ctg gac ccc gtg ctc tac tgc ttc tct       1112
Phe Thr Tyr Leu Asn Ser Val Leu Asp Pro Val Leu Tyr Cys Phe Ser
                345                 350                 355 agc ccc aac ttc ctc cac cag agc cgg gcc ttg ctg ggc ctc acg cgg       1160
```

```
Ser Pro Asn Phe Leu His Gln Ser Arg Ala Leu Leu Gly Leu Thr Arg
    360                 365                 370 ggc cgg cag ggc cca gtg agc gac gag agc tcc tac caa ccc tcc agg      1208
Gly Arg Gln Gly Pro Val Ser Asp Glu Ser Ser Tyr Gln Pro Ser Arg
375                 380                 385                 390 cag tgg cgc tac cgg gag gcc tct agg aag gcg gag gcc ata ggg aag      1256
Gln Trp Arg Tyr Arg Glu Ala Ser Arg Lys Ala Glu Ala Ile Gly Lys
                395                 400                 405 ctg aaa gtg cag ggc gag gtc tct ctg gaa aag gaa ggc tcc tcc cag      1304
Leu Lys Val Gln Gly Glu Val Ser Leu Glu Lys Glu Gly Ser Ser Gln
            410                 415                 420 ggc tgagggccag ctgcagggct gcagcgctgt gggggtaagg gctgccgcgc            1357
Gly tctggcctgg aggacaagg ccagcacacg gtgcctcaac caactggaca agggatggcg     1417
gcagaccagg ggccaggcca aagcactggc aggactcagg tgggt                    1462

<210> SEQ ID NO 2
<211> LENGTH: 423
<212> TYPE: PRT
<213> ORGANISM: Homo sapiens

<400> SEQUENCE: 2

Met Leu Cys His Arg Gly Gly Gln Leu Ile Val Pro Ile Ile Pro Leu
1               5                   10                  15

Cys Pro Glu His Ser Cys Arg Gly Arg Arg Leu Gln Asn Leu Leu Ser
                20                  25                  30

Gly Pro Trp Pro Lys Gln Pro Met Glu Leu His Asn Leu Ser Ser Pro
            35                  40                  45

Ser Pro Ser Leu Ser Ser Val Leu Pro Pro Ser Phe Ser Pro Ser
    50                  55                  60

Pro Ser Ser Ala Pro Ser Ala Phe Thr Thr Val Gly Gly Ser Ser Gly
65                  70                  75                  80

Gly Pro Cys His Pro Thr Ser Ser Leu Val Ser Ala Phe Leu Ala
                85                  90                  95

Pro Ile Leu Ala Leu Glu Phe Val Leu Gly Leu Val Gly Asn Ser Leu
            100                 105                 110

Ala Leu Phe Ile Phe Cys Ile His Thr Arg Pro Trp Thr Ser Asn Thr
        115                 120                 125

Val Phe Leu Val Ser Leu Val Ala Ala Asp Phe Leu Leu Ile Ser Asn
    130                 135                 140

Leu Pro Leu Arg Val Gly Tyr Tyr Leu Leu His Glu Thr Trp Arg Phe
145                 150                 155                 160

Gly Ala Ala Ala Cys Lys Val Asn Leu Phe Met Leu Ser Thr Asn Arg
                165                 170                 175

Thr Ala Ser Val Val Phe Leu Thr Ala Ile Ala Leu Asn Arg Tyr Leu
            180                 185                 190

Lys Val Val Gln Pro His His Val Leu Ser Arg Ala Ser Val Gly Ala
        195                 200                 205

Ala Ala Arg Val Ala Gly Gly Leu Trp Val Gly Ile Leu Leu Leu Asn
    210                 215                 220

Gly His Leu Leu Leu Ser Thr Phe Ser Gly Pro Ser Cys Leu Ser Tyr
225                 230                 235                 240

Arg Val Gly Thr Glu Pro Ser Ala Ser Leu Arg Trp His Gln Ala Leu
                245                 250                 255

Tyr Leu Leu Glu Phe Phe Leu Pro Leu Ala Leu Ile Leu Phe Ala Ile
```

-continued

```
                260                 265                 270
Val Ser Ile Gly Leu Thr Ile Arg Asn Arg Gly Leu Gly Gly Gln Ala
            275                 280                 285
Gly Pro Gln Arg Ala Met Arg Val Leu Ala Met Val Ala Val Tyr
        290                 295                 300
Thr Ile Cys Phe Leu Pro Ser Ile Ile Phe Gly Met Ala Ser Met Val
305                 310                 315                 320
Ala Phe Trp Leu Ser Ala Cys Arg Ser Leu Asp Leu Cys Ala Gln Leu
                325                 330                 335
Phe His Gly Ser Leu Ala Phe Thr Tyr Leu Asn Ser Val Leu Asp Pro
            340                 345                 350
Val Leu Tyr Cys Phe Ser Ser Pro Asn Phe Leu His Gln Ser Arg Ala
            355                 360                 365
Leu Leu Gly Leu Thr Arg Gly Arg Gln Gly Pro Val Ser Asp Glu Ser
        370                 375                 380
Ser Tyr Gln Pro Ser Arg Gln Trp Arg Tyr Arg Glu Ala Ser Arg Lys
385                 390                 395                 400
Ala Glu Ala Ile Gly Lys Leu Lys Val Gln Gly Glu Val Ser Leu Glu
                405                 410                 415
Lys Glu Gly Ser Ser Gln Gly
            420

<210> SEQ ID NO 3
<211> LENGTH: 267
<212> TYPE: PRT
<213> ORGANISM: Artificial
<220> FEATURE:
<223> OTHER INFORMATION: a query sequence
<220> FEATURE:
<221> NAME/KEY: UNCERTAIN
<222> LOCATION: (222)..(246)
<220> FEATURE:
<221> NAME/KEY: UNCERTAIN
<222> LOCATION: (101)..(199)
<220> FEATURE:
<221> NAME/KEY: UNCERTAIN
<222> LOCATION: (40)..(65)
<220> FEATURE:
<221> NAME/KEY: UNCERTAIN
<222> LOCATION: (75)..(75)

<400> SEQUENCE: 3

Ile Tyr Ser Ile Val Phe Val Val Gly Leu Leu Gly Asn Ala Leu Val
1               5                   10                  15
Ile Trp Val Leu Leu Arg His Lys Lys Met Arg Thr Val Thr Asn Ile
            20                  25                  30
Tyr Ile Leu Asn Leu Ala Ile Xaa Xaa Xaa Xaa Xaa Xaa Xaa Xaa
        35                  40                  45
Xaa Xaa Xaa Xaa Xaa Xaa Xaa Xaa Xaa Xaa Xaa Xaa Xaa Xaa Xaa
50                  55                  60
Xaa Leu Cys Lys Ile Val Ser Phe Leu Tyr Xaa Val Asn Met Tyr Ala
65                  70                  75                  80
Ser Ile Phe Thr Leu Thr Ala Ile Ser Ile Asp Arg Tyr Leu Ala Ile
                85                  90                  95
Val His Pro Leu Xaa Xaa Xaa Xaa Xaa Xaa Xaa Xaa Xaa Xaa Xaa
            100                 105                 110
Xaa Xaa Xaa Xaa Xaa Xaa Xaa Xaa Xaa Xaa Xaa Xaa Xaa Xaa Xaa
            115                 120                 125
Xaa Xaa Xaa Xaa Xaa Xaa Xaa Xaa Xaa Xaa Xaa Xaa Xaa Xaa Xaa
```

```
            130                 135                 140
Xaa Xaa Xaa Xaa Xaa Xaa Xaa Xaa Xaa Xaa Xaa Xaa Xaa Xaa
145                 150                 155                 160

Xaa Xaa Xaa Xaa Xaa Phe Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Arg Val Val Arg Met Ile Leu Val Val
        195                 200                 205

Val Val Val Phe Ala Ile Cys Trp Leu Pro Tyr His Ile Xaa Xaa Xaa
210                 215                 220

Xaa Xaa Xaa Xaa Xaa Xaa Xaa Xaa Xaa Xaa Ala Xaa Xaa Xaa Xaa
225                 230                 235                 240

Xaa Xaa Xaa Xaa Xaa Xaa Leu Ala Tyr Leu Asn Ser Cys Ile Asn Pro
            245                 250                 255

Ile Ile Tyr Ala Phe Leu Ser Lys Asn Phe Arg
        260                 265

<210> SEQ ID NO 4
<211> LENGTH: 795
<212> TYPE: DNA
<213> ORGANISM: Homo sapiens

<400> SEQUENCE: 4
atcctggccc tggagtttgt cctgggcctg gtggggaaca gtttggccct cttcatcttc      60
tgcatccaca cgcggccctg gacctccaac acggtgttcc tggtcagcct ggtggccgct     120
gacttcctcc tgatcagcaa cctgccctc gcgtggact actacctcct ccatgagacc      180
tggcgctttg gggctgctgc ctgcaaagtc aacctcttca tgctgtccac caaccgcacg     240
gccagcgttg tcttcctcac agccatcgca ctcaaccgct acctgaaggt ggtgcagccc     300
caccacgtgc tgagccgtgc ttccgtgggg gcagctgccc gggtggccgg ggactctgg     360 gtgggcatcc tgctcctcaa cgggcacctg ctcctgagca ccttctccgg ccctcctgc     420 ctcagctaca gggtgggcac gaagccctcg gcctcgctcc gctggcacca ggcactgtac     480
ctgctggagt tcttcctgcc actggcgctc atcctctttg ctattgtgag cattgggctc     540
accatccgga accgtggtct gggcgggcag gcaggcccgc agagggccat gcgtgtgctg     600
gccatggtgg tggccgtcta caccatctgc ttcttgccca gcatcatctt tggcatggct     660
tccatggtgg ctttctggct gtccgcctgc cgatccctgg acctctgcac acagctcttc     720
catggctccc tggccttcac ctacctcaac agtgtcctgg accccgtgct ctactgcttc     780
tctagcccca acttc                                                      795

<210> SEQ ID NO 5
<211> LENGTH: 1269
<212> TYPE: DNA
<213> ORGANISM: Homo sapiens

<400> SEQUENCE: 5
atgttgtgtc accgtggtgg ccagctgata gtgccaatca tcccactttg ccctgagcac      60
tcctgcaggg gtagaagact ccagaacctt ctctcaggcc catggcccaa gcagcccatg     120
gaacttcata acctgagctc tccatctccc tctctctcct cctctgttct cctccctcc     180 ttctctccct cacccctcctc tgctccctct gcctttacca ctgtgggggg gtcctctgga     240
gggccctgcc accccacctc ttcctcgctg gtgtctgcct tcctggcacc aatcctggcc     300
```

-continued

```
ctggagtttg tcctgggcct ggtggggaac agtttggccc tcttcatctt ctgcatccac    360
acgcggccct ggacctccaa cacggtgttc ctggtcagcc tggtggccgc tgacttcctc    420
ctgatcagca acctgcccct ccgcgtggac tactacctcc tccatgagac ctggcgcttt    480
ggggctgctg cctgcaaagt caacctcttc atgctgtcca ccaaccgcac ggccagcgtt    540
gtcttcctca cagccatcgc actcaaccgc tacctgaagg tggtgcagcc ccaccacgtg    600
ctgagccgtg cttccgtggg ggcagctgcc cgggtggccg ggggactctg ggtgggcatc    660
ctgctcctca cgggcacct gctcctgagc accttctccg cccctcctg cctcagctac     720 agggtgggca cgaagccctc ggcctcgctc cgctggcacc aggcactgta cctgctggag    780
ttcttcctgc cactggcgct catcctcttt gctattgtga gcattgggct caccatccgg    840
aaccgtggtc tgggcgggca ggcaggcccg cagagggcca tgcgtgtgct ggccatggtg    900
gtggccgtct acaccatctg cttcttgccc agcatcatct ttggcatggc ttccatggtg    960
gctttctggc tgtccgcctg ccgatccctg gacctctgca cacagctctt ccatggctcc    1020
ctggccttca cctacctcaa cagtgtcctg gaccccgtgc tctactgctt ctctagcccc    1080
aacttcctcc accagagccg ggccttgctg ggcctcacgc ggggccggca gggcccagtg    1140
agcgacgaga gctcctacca accctccagg cagtggcgct accggaggc ctctaggaag    1200 gcggaggcca tagggaagct gaaagtgcag ggcgaggtct ctctggaaaa ggaaggctcc    1260
tcccagggc                                                           1269
```

<210> SEQ ID NO 6
<211> LENGTH: 26
<212> TYPE: DNA
<213> ORGANISM: Artificial
<220> FEATURE:
<223> OTHER INFORMATION: artificially synthesized primer sequence

<400> SEQUENCE: 6
ttctcagtgg ctgcgagaat gctgat                                         26

<210> SEQ ID NO 7
<211> LENGTH: 26
<212> TYPE: DNA
<213> ORGANISM: Artificial
<220> FEATURE:
<223> OTHER INFORMATION: artificially synthesized primer sequence

<400> SEQUENCE: 7
acccacctga gtcctgccag tgcttt                                         26

<210> SEQ ID NO 8
<211> LENGTH: 31
<212> TYPE: DNA
<213> ORGANISM: Artificial
<220> FEATURE:
<223> OTHER INFORMATION: artificially synthesized primer sequence

<400> SEQUENCE: 8
agatctatgt tgtgtcaccg tggtggccag c                                   31

<210> SEQ ID NO 9
<211> LENGTH: 38
<212> TYPE: DNA
<213> ORGANISM: Artificial
<220> FEATURE:
<223> OTHER INFORMATION: artificially synthesized primer sequence

<400> SEQUENCE: 9
aagcttcggt ccgccctggg aggagccttc cttttcca                                    38

<210> SEQ ID NO 10
<211> LENGTH: 22
<212> TYPE: DNA
<213> ORGANISM: Artificial
<220> FEATURE:
<223> OTHER INFORMATION: artificially synthesized primer sequence

<400> SEQUENCE: 10
gctttcggca ccatgggctg ca                                                     22

<210> SEQ ID NO 11
<211> LENGTH: 25
<212> TYPE: DNA
<213> ORGANISM: Artificial
<220> FEATURE:
<223> OTHER INFORMATION: artificially synthesized primer sequence

<400> SEQUENCE: 11
tcacactgca ggaccatctg tcaca                                                  25

<210> SEQ ID NO 12
<211> LENGTH: 31
<212> TYPE: DNA
<213> ORGANISM: Artificial
<220> FEATURE:
<223> OTHER INFORMATION: artificially synthesized primer sequence

<400> SEQUENCE: 12
tctagacgga ccgatgggct gcacgctgag c                                           31

<210> SEQ ID NO 13
<211> LENGTH: 33
<212> TYPE: DNA
<213> ORGANISM: Artificial
<220> FEATURE:
<223> OTHER INFORMATION: artificially synthesized primer sequence

<400> SEQUENCE: 13
ggatccttaa aagagaccaa tatcttttag att                                         33

<210> SEQ ID NO 14
<211> LENGTH: 23
<212> TYPE: DNA
<213> ORGANISM: Artificial
<220> FEATURE:
<223> OTHER INFORMATION: artificially synthesized primer sequence

<400> SEQUENCE: 14
gagcgaggcg ggagggtgtg tgt                                                    23

<210> SEQ ID NO 15
<211> LENGTH: 23
<212> TYPE: DNA
<213> ORGANISM: Artificial
<220> FEATURE:
<223> OTHER INFORMATION: artificially synthesized primer sequence

<400> SEQUENCE: 15
gaagggcagg gcgggtgtct agc                                                    23

<210> SEQ ID NO 16
<211> LENGTH: 31

<210> SEQ ID NO 16
<211> LENGTH: 31
<212> TYPE: DNA
<213> ORGANISM: Artificial
<220> FEATURE:
<223> OTHER INFORMATION: artificially synthesized primer sequence

<400> SEQUENCE: 16
ttcggaccga tgactctgga gtccatcatg g                                31

<210> SEQ ID NO 17
<211> LENGTH: 33
<212> TYPE: DNA
<213> ORGANISM: Artificial
<220> FEATURE:
<223> OTHER INFORMATION: artificially synthesized primer sequence

<400> SEQUENCE: 17
agggatcctt agaccagatt gtactccttc agg                              33

<210> SEQ ID NO 18
<211> LENGTH: 34
<212> TYPE: DNA
<213> ORGANISM: Artificial
<220> FEATURE:
<223> OTHER INFORMATION: artificially synthesized primer sequence

<400> SEQUENCE: 18
gccggaccga tgggctgcct cgggaacagt aaga                             34

<210> SEQ ID NO 19
<211> LENGTH: 33
<212> TYPE: DNA
<213> ORGANISM: Artificial
<220> FEATURE:
<223> OTHER INFORMATION: artificially synthesized primer sequence

<400> SEQUENCE: 19
gctctagaat ttgggggttc ccttcttaga gca                              33

<210> SEQ ID NO 20
<211> LENGTH: 1462
<212> TYPE: DNA
<213> ORGANISM: Homo sapiens
<220> FEATURE:
<221> NAME/KEY: CDS
<222> LOCATION: (39)...(1307)
<223> OTHER INFORMATION:

<400> SEQUENCE: 20

| | | | | | |
|---|---|---|---|---|---|
| ttctcagtgg ctgcgagaat gctgatgaaa accccagg | atg | ttg | tgt | cac | cgt | ggt | 56 |
| | Met | Leu | Cys | His | Arg | Gly |
| | 1   |     |     |     | 5   |     | ggc cag ctg ata gtg cca atc atc cca ctt tgc cct gag cac tcc tgc     104
Gly Gln Leu Ile Val Pro Ile Ile Pro Leu Cys Pro Glu His Ser Cys
        10                  15                  20 agg ggt aga aga ctc cag aac ctt ctc tca ggc cca tgg ccc aag cag     152
Arg Gly Arg Arg Leu Gln Asn Leu Leu Ser Gly Pro Trp Pro Lys Gln
    25                  30                  35 ccc atg gaa ctt cat aac ctg agc tct cca tct ccc tct ctc tcc tcc     200
Pro Met Glu Leu His Asn Leu Ser Ser Pro Ser Pro Ser Leu Ser Ser
40                  45                  50 tct gtt ctc cct ccc tcc ttc tct ccc tca ccc tcc tct gct ccc tct     248
Ser Val Leu Pro Pro Ser Phe Ser Pro Ser Pro Ser Ser Ala Pro Ser
55                  60                  65                  70 gcc ttt acc act gtg ggg ggg tcc tct gga ggg ccc tgc cac ccc acc     296
Ala Phe Thr Thr Val Gly Gly Ser Ser Gly Gly Pro Cys His Pro Thr -continued

|   | 75 |   |   |   | 80 |   |   |   | 85 |   |   |   |   |   |
|---|---|---|---|---|---|---|---|---|---|---|---|---|---|---|
| tct | tcc | tcg | ctg | gtg | tct | gcc | ttc | ctg | gca | cca | atc | ctg | gcc | ctg | gag | 344 |
| Ser | Ser | Ser | Leu | Val | Ser | Ala | Phe | Leu | Ala | Pro | Ile | Leu | Ala | Leu | Glu |   |
|   |   |   | 90 |   |   |   |   | 95 |   |   |   | 100 |   |   |   |   | ttc gtc ctg ggc ctg gtg ggg aac agt ttg gcc ctc ttc atc ttc tgc    392
Phe Val Leu Gly Leu Val Gly Asn Ser Leu Ala Leu Phe Ile Phe Cys
            105                 110                 115 atc cac acg cgg ccc tgg acc tcc aac acg gtg ttc ctg gtc agc ctg    440
Ile His Thr Arg Pro Trp Thr Ser Asn Thr Val Phe Leu Val Ser Leu
        120                 125                 130 gtg gcc gct gac ttc ctc ctg atc agc aac ctg ccc ctc cgc gtg gac    488
Val Ala Ala Asp Phe Leu Leu Ile Ser Asn Leu Pro Leu Arg Val Asp
135                 140                 145                 150 tac tac ctc ctc cat gag acc tgg cgc ttt ggg gct gct gcc tgc aaa    536
Tyr Tyr Leu Leu His Glu Thr Trp Arg Phe Gly Ala Ala Ala Cys Lys
                155                 160                 165 gtc aac ctc ttc atg ctg tcc acc aac cgc acg gcc agc gtt gtc ttc    584
Val Asn Leu Phe Met Leu Ser Thr Asn Arg Thr Ala Ser Val Val Phe
            170                 175                 180 ctc aca gcc atc gca ctc aac cgc tac ctg aag gtg gtg cag ccc cac    632
Leu Thr Ala Ile Ala Leu Asn Arg Tyr Leu Lys Val Val Gln Pro His
        185                 190                 195 cac gtg ctg agc cgt gct tcc gtg ggg gca gct gcc cgg gtg gcc ggg    680
His Val Leu Ser Arg Ala Ser Val Gly Ala Ala Ala Arg Val Ala Gly
200                 205                 210 gga ctc tgg gtg ggc atc ctc ctc aac ggg cac ctg ctc ctg agc       728
Gly Leu Trp Val Gly Ile Leu Leu Asn Gly His Leu Leu Leu Ser
215                 220                 225                 230 acc ttc tcc ggc ccc tcc tgc ctc agc tac agg gtg ggc acg aag ccc    776
Thr Phe Ser Gly Pro Ser Cys Leu Ser Tyr Arg Val Gly Thr Lys Pro
            235                 240                 245 tcg gcc tcg ctc cgc tgg cac cag gca ctg tac ctg ctg gag ttc ttc    824
Ser Ala Ser Leu Arg Trp His Gln Ala Leu Tyr Leu Leu Glu Phe Phe
        250                 255                 260 ctg cca ctg gcg ctc atc ctc ttt gct att gtg agc att ggg ctc acc    872
Leu Pro Leu Ala Leu Ile Leu Phe Ala Ile Val Ser Ile Gly Leu Thr
                265                 270                 275 atc cgg aac cgt ggt ctg ggc ggg cag gca ggc ccg cag agg gcc atg    920
Ile Arg Asn Arg Gly Leu Gly Gly Gln Ala Gly Pro Gln Arg Ala Met
            280                 285                 290 cgt gtg ctg gcc atg gtg gtg gcc gtc tac acc atc tgc ttc ttg ccc    968
Arg Val Leu Ala Met Val Val Ala Val Tyr Thr Ile Cys Phe Leu Pro
295                 300                 305                 310 agc atc atc ttt ggc atg gct tcc atg gtg gct ttc tgg ctg tcc gcc   1016
Ser Ile Ile Phe Gly Met Ala Ser Met Val Ala Phe Trp Leu Ser Ala
        315                 320                 325 tgc cga tcc ctg gac ctc tgc aca cag ctc ttc cat ggc tcc ctg gcc   1064
Cys Arg Ser Leu Asp Leu Cys Thr Gln Leu Phe His Gly Ser Leu Ala
                330                 335                 340 ttc acc tac ctc aac agt gtc ctg gac ccc gtg ctc tac tgc ttc tct   1112
Phe Thr Tyr Leu Asn Ser Val Leu Asp Pro Val Leu Tyr Cys Phe Ser
            345                 350                 355 agc ccc aac ttc ctc cac cag agc cgg gcc ttg ctg ggc ctc acg cgg   1160
Ser Pro Asn Phe Leu His Gln Ser Arg Ala Leu Leu Gly Leu Thr Arg
        360                 365                 370 ggc cgg cag ggc cca gtg agc gac gag agc tcc tac caa ccc tcc agg   1208
Gly Arg Gln Gly Pro Val Ser Asp Glu Ser Ser Tyr Gln Pro Ser Arg
375                 380                 385                 390 cag tgg cgc tac cgg gag gcc tct agg aag gcg gag gcc ata ggg aag   1256

```
Gln Trp Arg Tyr Arg Glu Ala Ser Arg Lys Ala Glu Ala Ile Gly Lys
                395                 400                 405 ctg aaa gtg cag ggc gag gtc tct ctg gaa aag gaa ggc tcc tcc cag        1304
Leu Lys Val Gln Gly Glu Val Ser Leu Glu Lys Glu Gly Ser Ser Gln
            410                 415                 420 ggc tgagggccag ctgcagggct gcagcgctgt gggggtaagg gctgccgcgc             1357
Gly tctggcctgg agggacaagg ccagcacacg gtgcctcaac caactggaca agggatggcg      1417
gcagaccagg ggccaggcca aagcactggc aggactcagg tgggt                     1462

<210> SEQ ID NO 21
<211> LENGTH: 423
<212> TYPE: PRT
<213> ORGANISM: Homo sapiens

<400> SEQUENCE: 21

Met Leu Cys His Arg Gly Gly Gln Leu Ile Val Pro Ile Ile Pro Leu
1               5                   10                  15

Cys Pro Glu His Ser Cys Arg Gly Arg Arg Leu Gln Asn Leu Leu Ser
            20                  25                  30

Gly Pro Trp Pro Lys Gln Pro Met Glu Leu His Asn Leu Ser Ser Pro
        35                  40                  45

Ser Pro Ser Leu Ser Ser Val Leu Pro Pro Ser Phe Ser Pro Ser
    50                  55                  60

Pro Ser Ser Ala Pro Ser Ala Phe Thr Thr Val Gly Gly Ser Ser Gly
65                  70                  75                  80

Gly Pro Cys His Pro Thr Ser Ser Leu Val Ser Ala Phe Leu Ala
                85                  90                  95

Pro Ile Leu Ala Leu Glu Phe Val Leu Gly Leu Val Gly Asn Ser Leu
            100                 105                 110

Ala Leu Phe Ile Phe Cys Ile His Thr Arg Pro Trp Thr Ser Asn Thr
        115                 120                 125

Val Phe Leu Val Ser Leu Val Ala Ala Asp Phe Leu Leu Ile Ser Asn
    130                 135                 140

Leu Pro Leu Arg Val Asp Tyr Tyr Leu Leu His Glu Thr Trp Arg Phe
145                 150                 155                 160

Gly Ala Ala Ala Cys Lys Val Asn Leu Phe Met Leu Ser Thr Asn Arg
                165                 170                 175

Thr Ala Ser Val Val Phe Leu Thr Ala Ile Ala Leu Asn Arg Tyr Leu
            180                 185                 190

Lys Val Val Gln Pro His His Val Leu Ser Arg Ala Ser Val Gly Ala
        195                 200                 205

Ala Ala Arg Val Ala Gly Gly Leu Trp Val Gly Ile Leu Leu Leu Asn
    210                 215                 220

Gly His Leu Leu Leu Ser Thr Phe Ser Gly Pro Ser Cys Leu Ser Tyr
225                 230                 235                 240

Arg Val Gly Thr Lys Pro Ser Ala Ser Leu Arg Trp His Gln Ala Leu
                245                 250                 255

Tyr Leu Leu Glu Phe Phe Leu Pro Leu Ala Leu Ile Leu Phe Ala Ile
            260                 265                 270

Val Ser Ile Gly Leu Thr Ile Arg Asn Arg Gly Leu Gly Gly Gln Ala
        275                 280                 285

Gly Pro Gln Arg Ala Met Arg Val Leu Ala Met Val Val Ala Val Tyr
    290                 295                 300
```

```
                                          -continued
Thr Ile Cys Phe Leu Pro Ser Ile Ile Phe Gly Met Ala Ser Met Val
305                 310                 315                 320

Ala Phe Trp Leu Ser Ala Cys Arg Ser Leu Asp Leu Cys Thr Gln Leu
                325                 330                 335

Phe His Gly Ser Leu Ala Phe Thr Tyr Leu Asn Ser Val Leu Asp Pro
            340                 345                 350

Val Leu Tyr Cys Phe Ser Ser Pro Asn Phe Leu His Gln Ser Arg Ala
        355                 360                 365

Leu Leu Gly Leu Thr Arg Gly Arg Gln Gly Pro Val Ser Asp Glu Ser
    370                 375                 380

Ser Tyr Gln Pro Ser Arg Gln Trp Arg Tyr Arg Glu Ala Ser Arg Lys
385                 390                 395                 400

Ala Glu Ala Ile Gly Lys Leu Lys Val Gln Gly Glu Val Ser Leu Glu
                405                 410                 415

Lys Glu Gly Ser Ser Gln Gly
            420

<210> SEQ ID NO 22
<211> LENGTH: 24
<212> TYPE: DNA
<213> ORGANISM: Artificial Sequence
<220> FEATURE:
<223> OTHER INFORMATION: sense primer

<400> SEQUENCE: 22
tccctctgcc tttaccactg tggg                                          24

<210> SEQ ID NO 23
<211> LENGTH: 23
<212> TYPE: DNA
<213> ORGANISM: Artificial Sequence
<220> FEATURE:
<223> OTHER INFORMATION: antisense primer

<400> SEQUENCE: 23
gtaggagctc tcgtcgctca ctg                                           23
```

# G-PROTEIN COUPLED RECEPTOR HAVING EICOSANOID AS LIGAND AND GENE THEREOF

This application is a continuation-in-part of co-pending PCT International Application No. PCT/JP03/03042 filed on Mar. 14, 2003, which designated the United States, which claims priority under 35 U.S.C. § 119(a) on Patent Application No.2002-075724 filed in Japan on Mar. 19, 2002, and also claims the benefit of Provisional Application No. 60/517,919, filed on Nov. 7, 2003, on which priority is claimed under 35U.S.C. § 119(e). The entire contents of No. PCT/JP03/03042 and No. 60/517,919 are hereby incorporated by reference.

BACKGROUND OF THE INVENTION

1. Field of the Invention

The present invention relates to a protein of a G-protein coupled receptor having an eicosanoid as a ligand (more specifically, 5-oxo-6E, 8Z,11Z,14Z-eicosatetraenoic acid, hereinafter referred to as 5-oxo-ETE), or a gene thereof. The present invention also relates to a process for screening a candidate for a pharmaceutical compound, using the same. Further, the present invention relates to a pharmaceutical composition comprising an antagonist of the receptor, and to a method for treatment, etc. using the antagonist.

2. Background Art

Physiologically active substances such as many neurotransmitters, hormones, autacoids, etc. regulate biological functions through interactions with specific receptors which exist on the cell surface. Most of these receptors are coupled with a GTP-binding protein (hereinafter referred to as G-protein), which is a trimeric protein existing in a cell, and it has been known that signals are transduced intracellularly via an activation of the G-protein. These receptors therefore are generally referred to as G-protein coupled receptors. Any of the G-protein coupled receptors are known to share a common structure including 7 transmembrane domains.

The G-protein is a trimeric protein consisting of α, β and γ subunits, and in a ground state, it exists as an inactivated form (GDP-binding form) in which these subunits are associated. By the G-protein coupled receptor which has been stimulated by a ligand, the inactivated form (GDP-binding form) of the G-protein is converted to an activated form (GTP-binding form), and it is dissociated into an a subunit (Gα) which is bound to GTP, and a β/γ subunit complex (Gβγ). Then, the GTP-binding α subunit (Gα) (or occasionally Gβγ) controls effectors such as adenlylate cyclase, phospholipase C, etc., to transduce signals.

Further, the G-protein, especially Gα, has a variety and it is known that different kinds of effectors are regulated depending on the kinds of Gα. In general, the G-protein coupled receptor activates a specific type of G-protein, through which a specific type of signal transduction is made intracellularly.

As the G-protein coupled receptor, there have been known α- and β-adrenaline receptors, muscarinic acetylcholine receptors, adenosine receptors, angiotensin receptors, endothelin receptors, gonadotropin-releasing factor receptors, H1- and H2-histamine receptors, dopamine receptors, metabotropic glutamate receptors, somatostatin receptors, etc.

Each of the above receptors plays an important roll in vivo, as a target of physiologically active substances. Moreover, it is a significant fact that many of the medicaments which have been known to date are ligands, or agonists and antagonists whose targets are the G-protein coupled receptors.

From these facts, the G-protein coupled receptors have been drawing attention as a target of research and development of the pharmaceuticals. It has been earnestly desired to find out a novel G-protein coupled receptor, to identify a ligand thereof, and to find out a method for screening or identifying the agonists and antagonists thereof, since they lead to screening of a novel candidate for pharmaceutical compound.

With respect to the eicosanoid receptors, the followings have been known. Those generally referred to as eicosanoids include prostaglandin, prostacyclin, thromboxanthine, leukotriene, and an eicosatetraenoic acid such as 5-oxo-ETE, 5-hydroxyeicosa-6E,8Z,11Z,14Z-tetraenoic acid (5-HETE), etc. As the receptors having eicosanoid as a ligand, there has been reported prostaglandin EP1, EP2, EP3, EP4, F2α receptor, prostacyclin PI2 receptor, thromboxanthine TA2 receptor, leukotriene B4 receptor, which are all G-protein coupled receptors (Narumiya, et al., Physiol. Rev., Vol. 79, pp. 1193-1226, 1999; Mohammed Akbar, et al., J. Biol. Chem., vol. 271, pp. 18363-18367, 1996). However, a receptor having an eicosatetraenoic acid such as 5-oxo-ETE and eicosatrienoic acid as a ligand which has been identified in the present invention has not been reported to date.

Further, with respect to the 5-oxo-ETE, (5-oxo-6E,8Z,11Z, 14Z-eicosatetraenoic acid), the followings have been known.

5-Oxo-ETE is a substance derived from a fatty acid having 20 carbon atoms, such as an eicosanoic acid, and it is synthesized from arachidonic acid which is a biosynthetic intermediate of prostaglandin and leukotriene, through 5-HETE (see FIG. 1 below).

It has been known that 5-oxo-ETE induces eosinophil and neutrophil migration (Schwenk, et al., J. Biol. Chem., Vol. 270, pp. 15029-15036, 1995; Guilbert, et al., Am. J. Respir. Cell Mol. Biol.,Vol. 21, pp. 97-104, 1999; Stamatiou, et al., J. Clin. Invest., Vol. 102, pp. 2165-2172, 1998).

It has been known that 5-oxo-ETE is a growth factor and a maintenance factor of prostate cancer, breast cancer, lung cancer, pancreas cancer, and mesothelioma, and inhibition of the synthesis of the same will lead to apoptosis (Ghosh, et al., Biochem. Biophys. Res. Commun., Vol. 235, pp. 418-423, 1997; Ghosh, et al., Proc. Natl. Acad. Sci. USA, Vol. 95, pp. 13182-13187, 1998; Avis, et al., FASEB J., Vol. 15, pp. 2007-2009, 2001; Avis et al., J. Clin. Invest., Vol. 97, pp. 806-813, 1996; Ding, et al., Biochem. Biophys. Res. Commun., Vol. 261, pp. 218-223, 1999; Romano, et al., FASEB J. Vol. 15, pp. 2326-2336, 2001).

An object of the present invention is to provide a G-protein coupled receptor having eicosanoid as a ligand, and a gene thereof.

Further, an object of the present invention is to provide a method for screening, identifying, and characterizing a ligand and an effector (an agonist or an antagonist) for the receptor protein.

Further, an object of the present invention is to provide a novel method for treatment, etc., using an antagonist of the receptor (the G-protein coupled receptor having an eicosanoid such as 5-oxo-ETE as a ligand).

The present inventors have isolated a full length human cDNA encoding a novel G-protein coupled receptor (hereinafter also referred to as TG1019). Moreover, they have successfully expressed the receptor protein in the cell, using recombinant DNA technology. Further, they have identified a ligand for the receptor, and have found out that the receptor has an eicosanoid (5-oxo-ETE, etc.) as a ligand (Hosoi, et al., J. Biol. Chem., Vol. 277, pp. 31459-31465, 2002).

In addition, the present inventors have found out that migration of eosinophils and neutrophils by 5-oxo ETE are

SUMMARY OF THE INVENTION

The present invention relates to a polypeptide selected from the following (A), (B) and (C), having a function or an activity as a receptor of an eicosanoid (5-oxo-ETE, etc.);

(A) a polypeptide comprising an amino acid sequence shown by SEQ ID NO:2 or SEQ ID NO:21;

(B) a polypeptide comprising an amino acid sequence shown by SEQ ID NO: 2 or SEQ.ID.NO:21 in which one or several amino acids are deleted, substituted or added;

(C) a polypeptide encoded by a nucleic acid which hybridizes under stringent condition with a nucleic acid comprising a nucleotide sequence shown by SEQ ID NO:1 or SEQ ID NO:20 or a complement thereof.

The present invention also relates to a nucleic acid encoding the above polypeptide.

Yet further, the present invention relates to a recombinant vector and a host cell, comprising the above nucleic acid.

Still further, the present invention relates to a method for detecting a function or an activity of the polypeptide, using the same. Still more, the present invention relates to a method for modulating (promoting or inhibiting) a function or an activity of said polypeptide, using the same.

The present invention further relates to a method for screening or identifying a ligand or an effector (an agonist or an antagonist) of said polypeptide, using the same.

The present invention also relates to a pharmaceutical composition comprising as an effective ingredient an antagonist of said polypeptide (a G-protein coupled receptor having an eicosanoid such as 5-oxo-ETE as a ligand), and to a method for treating and preventing diseases, comprising administering an effective amount of the antagonist to a patient.

Further, the present invention relates to a method for (1) inhibiting migration of eosinophils and neutrophils, or (2) inducing apoptosis in cancer cell, comprising the step of administering an antagonist of said polypeptide (a G-protein coupled receptor having an eicosanoid such as 5-oxo-ETE as a ligand).

The receptor protein or polypeptide (a G-protein coupled receptor having an eicosanoid such as 5-oxo-ETE as a ligand) is also referred to as "TG1019" hereinafter.

BRIEF DESCRIPTIONS OF THE DRAWINGS

FIG. 2 shows an amino acid sequence SEQ ID NO:2, a nucleotide sequence SEQ ID NO:1 and presumed 7 transmembrane domains (underlined) of TG1019.

FIG. 3 shows an expression pattern of TG1019 gene (a result of dot blotting) in respective tissues and cells in human.

In FIG. 5A to FIG. 5H, the specific binding amounts are shown by a relative value (% to control), based on the binding amount in the control where no test compound was added. "○ $G_{i\alpha1}$ (351Cys→Ile)" shows a test result in a membrane fraction containing a fusion protein of TG1019 protein and $G_{i\alpha1}$ (351Cys→Ile). "Δ $G_{q\alpha}$" shows a test result in a membrane fraction containing a fusion protein of TG1019 protein and $G_{q\alpha}$. "□ $G_{s\alpha L}$" shows a test result in a membrane fraction containing a fusion protein of TG1019 protein and $G_{s\alpha L}$.

Figure 6:
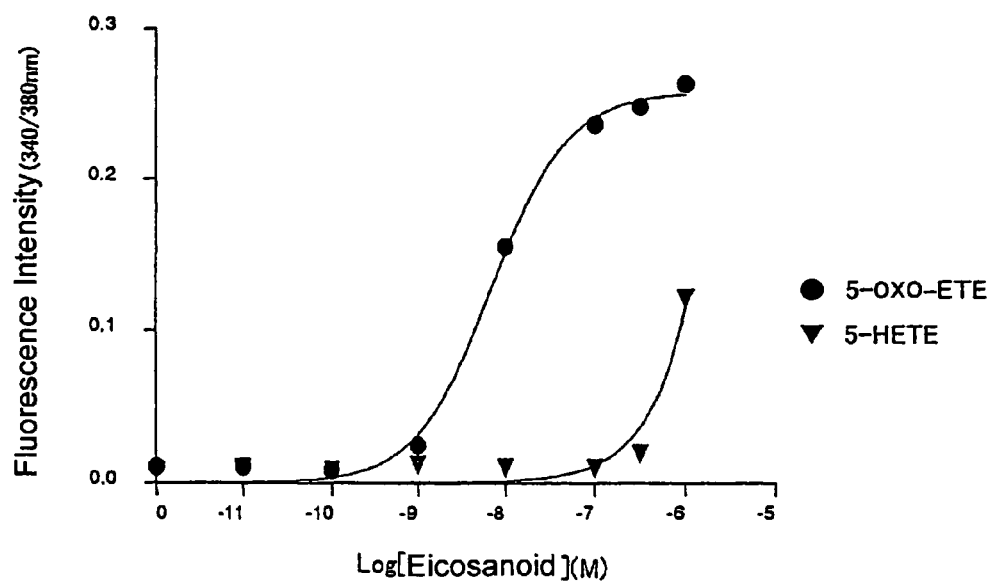

FIG. 6 shows a change in intercellular calcium levels in cells stably expressing TG1019 (5-oxo-ETE receptor) upon stimulation by 5-oxo ETE or 5-HETE. The calcium levels are shown by ratio of fluorescence intensities of 340 nm and 380 nm. "●" and "▼" respectively show the test results of 5-oxo-ETE and 5-HETE.

Figure 7:
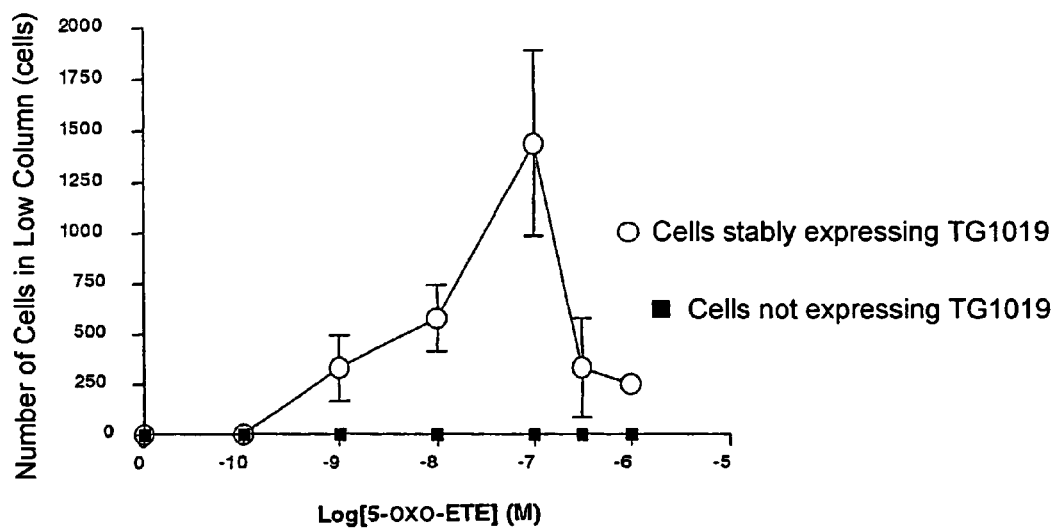

FIG. 7 shows 5-oxo-ETE-induced migrations of cells stably expressing TG1019 (5-oxo-ETE receptor) and those not expressing the same. "○" shows numbers of migrated cells in TG1019 stably expressing cells and "■" shows numbers of migrated cells in cells not expressing TG1019.

Figure 8A:
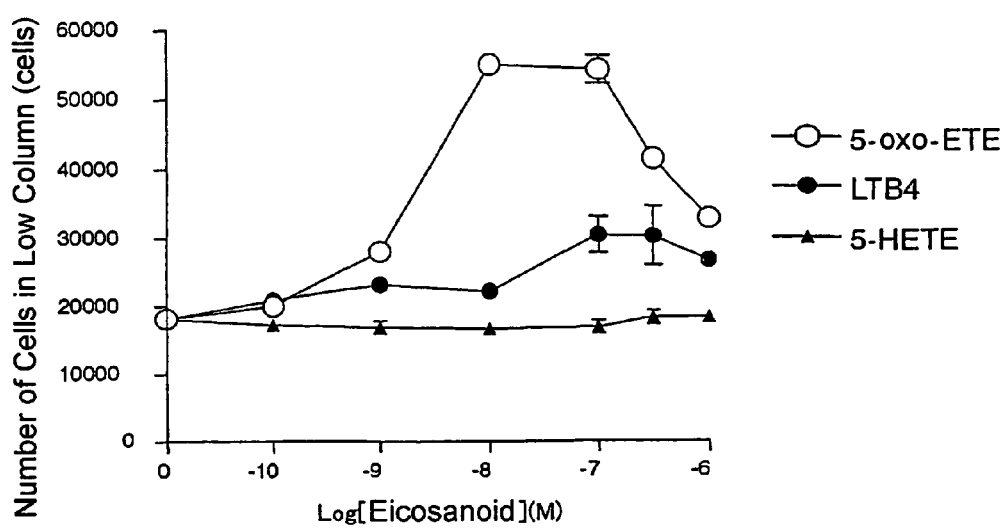

FIG. 8A shows migrations of eosinophils induced by 5-oxo-ETE, LTB4, or 5-HETE. "○" shows numbers of migrated cells induced by 5-oxo-ETE, "●" shows numbers of migrated cells induced by LTB4, and "▲" shows numbers of migrated cells induced by 5-HETE.

Figure 8B:
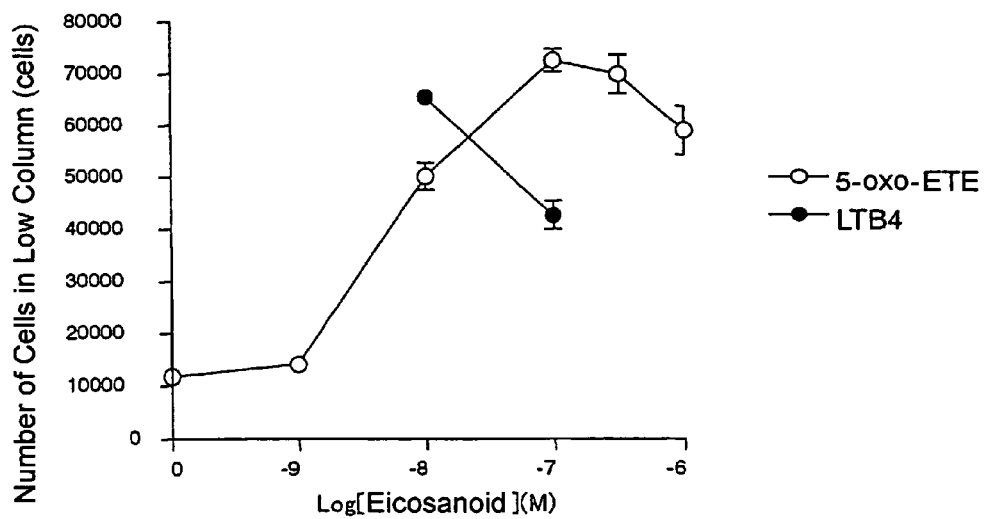

FIG. 8B shows migrations of neutrophils induced by 5-oxo-ETE or LTB4. "○" shows numbers of migrated cells induced by 5-oxo-ETE and "●" shows numbers of migrated cells induced by LTB4.

Figure 9:
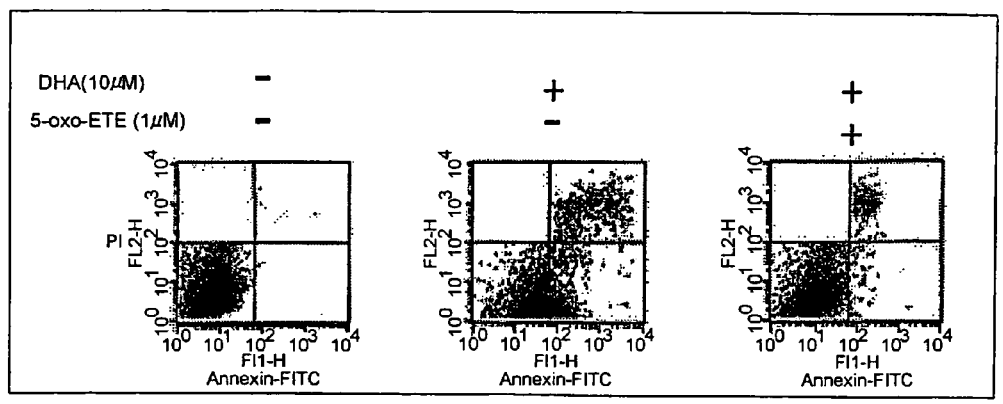

FIG. 9 shows an apoptosis inducing effect of docosahexaenoic acid (DHA) on PC3 prostate cancer cells.

DETAILED DESCRIPTION OF THE INVENTION

SEQ ID NO: 1 of the sequence listing mentioned below, shown in FIG. 2 represents a nucleotide sequence of a human cDNA (covering an entire coding region) of a gene (referred to as TG1019 gene) of the receptor protein (referred to as TG1019 protein) isolated by the present inventors. SEQ ID NO: 2 shown in FIG. 2 represents an amino acid sequence of the receptor protein (TG1019 protein) encoded by said cDNA.

The receptor protein of the present invention is a G-protein coupled receptor protein, which has a function (a biological activity) as a receptor of eicosanoids (e.g., 5-oxo-ETE). Therefore, the receptor protein of the present invention specifically binds to eicosanoids. By the specific binding of eicosanoids and the receptor protein of the present invention, the receptor protein is stimulated, whereby an intracellular signal transduction is induced.

The eicosanoid, a ligand of the receptor protein of the present invention, means a substance derived from a fatty acid having 20 carbon atoms, such as eicosanoic acid, and preferably, a fatty acid in which $8^{th}$ position is unsaturated. More specifically, it includes, in addition to 5-oxo-6E,8Z,11Z,14Z-eicosatetraenoic acid (referred to as 5-oxo-ETE) and 5-hydroxyeicosa-6E,8Z,11Z, 14z-tetraenoic acid (referred to as 5-HETE), 5-hydroperoxyeicosa-6E,8Z,11Z,14Z-tetraenoic acid (referred to as 5-HPETE), arachidonic acid (or eicosa-5Z,8Z,11Z,14Z-tetraenoic acid), eicosa-5Z,8Z,11Z-trienoic acid, 5-hydroxyeicosa-6E,8Z,11Z-trienoic acid (referred to as 5-HETrE), eicosa-5Z,8Z-dienoic acid, and 5,8,11-eicosatriynoic acid (referred to as ETI).

Upon stimulation by a ligand (an agonist), the receptor protein of the present invention activates a G-protein which belongs to a $G_i$ subfamily. When a subunit is focused on, the receptor protein of the present invention converts $G_{i\alpha}$ (an α subunit of G-protein belonging to $G_i$ subfamily, e.g., $G_{i\alpha1}$) into an activated form (a state having a GTP-binding ability), upon stimulation by a ligand (an agonist). Through the activation of the G-protein, intracellular signals can be transduced.

As stated above, the receptor protein (polypeptide) of the present invention has the following functions (i) to (iii):
 (i) Specific binding to a ligand,
 (ii) Induction of intracellular signal transductions (change in $Ca^{2+}$ level, change in cAMP level, activation of phospholipase C, change in pH, change in $K^+$ level, etc.) based on the stimulation by a ligand which acts as an agonist, and
 (iii) Activation of G-protein (an α subunit of a G-protein belonging to $G_i$ subfamily) based on the stimulation by a ligand which acts as an agonist.

As the ligand which acts as an agonist includes, for example, eicosanoids such as 5-oxo-ETE, 5-HPETE, arachidonic acid, eicosa-5Z,8Z,11Z-trienoic acid, 5-HETrE, eicosa-5Z,8Z-dienoic acid, 5-HETE, ETI, etc., among which 5-oxo-ETE is mentioned as a particularly preferred example.

In the present invention, "ligand" means a compound having an ability to specifically bind to the receptor protein. The ligand includes both of natural compound and artificially synthesized compound.

In the present invention, "agonist" means a compound having an ability to induce intracellular signal transduction through stimulation of a receptor protein, by specifically binding to the receptor protein, etc.

Further, in the present invention, "antagonist" means a compound having an ability to inhibit an intracellular signal transduction which has been triggered by a stimulation of the receptor protein by an agonist.

The protein or the polypeptide of the present invention includes those comprising an amino acid sequence shown by SEQ ID NO:2 or SEQ ID NO:21. In addition, the polypeptide comprising an amino acid sequence shown by SEQ ID NO:2 or SEQ ID NO:21, in which one or more amino acids are deleted, substituted, or added are also included.

Deletion, substitution and addition of the amino acids are admitted as long as the function (biological activity) as an receptor of an eicosanoid (5-oxo-ETE, etc.) is not lost, and normally, it is from 1 to about 80, preferably, from 1 to about 60, and more preferably, from 1 to about 45, further more preferably, from 1 to about 30, and still further preferably, from 1 to about 15.

Accordingly, the protein or the polypeptide of the present invention includes, in addition to the polypeptide comprising an amino acid sequence shown by SEQ ID NO:2 or SEQ ID NO:21, a polypeptide having one or more conservative amino acid substitution, as compared to the polypeptide comprising an amino acid sequence shown by SEQ ID NO:2 or SEQ ID NO:21.

Such protein or polypeptide includes, in addition to a naturally-occurring mutated form of protein or polypeptide, an artificially modified variant protein or polypeptide, a protein or polypeptide derived from a different living species, etc.

Accordingly, such protein or polypeptide includes conservative substitution variants and naturally-occurring allelic variants of the polypeptide comprising an amino acid sequence shown by SEQ ID NO:2 or SEQ ID NO:21.

Such protein or polypeptide has a homology with an amino acid sequence shown by SEQ ID NO: 2 or SEQ ID NO:21, by normally about 75% or more, preferably about 80% or more, more preferably about 85% or more, further more preferably about 90% or more, and yet more preferably about 95% or more.

The nucleic acid (DNA or RNA) of the present invention includes a nucleic acid comprising a nucleotide sequence shown by SEQ ID NO:1 or SEQ ID NO:20. In addition, there is mentioned a nucleic acid which hybridizes with the nucleic acid comprising a nucleotide sequence shown by SEQ ID NO:1 or SEQ ID NO:20 under stringent condition (more preferably under highly stringent condition), or a complement thereof (in other words, a nucleic acid comprising a complementary sequence thereof). Such nucleic acid is not limited, as long as it encodes a protein or a polypeptide which has a function (a biological activity) as a receptor of an eicosanoid (5-oxo-ETE, etc.).

Such nucleic acid has a homology with the nucleotide sequence shown by SEQ ID NO: 1 or SEQ ID NO:20, by normally about 70% or more, preferably about 80% or more, more preferably about 85% or more, further more preferably about 90% or more, and yet more preferably about 95% or more. Such gene or nucleic acid includes a naturally-occurring mutant gene, an artificially modified mutant gene, a homologous gene derived from a different living species (orthologue), etc.

In the present invention, hybridization under a stringent condition usually means hybridization carried out by hybridizing in 6×SSC or in a hybridization solution having a salt concentration equivalent to 6×SSC, at a temperature condition of 50 to 60° C. for about 16 hours, optionally followed by preliminary washing with 6×SSC or with a solution having a salt concentration equivalent to 6×SSC, and then subjecting to washing in 1×SSC or in a solution having a salt concentration equivalent to 1×SSC. Also, in case of hybridization under a condition with a higher stringency (or under highly stringent condition), the above-mentioned washing is carried out in 0.1×SSC or in a solution having a salt concentration equivalent to 0.1×SSC.

Sequence homologies can be analyzed by a conventional method, for example, Blast Method (Altschul, et al., J. Mol. Biol., Vol. 215, pp. 403-410, 1990).

The nucleic acid of the present invention can be isolated by screening tissues or cells of mammals as a genetic source. As mammals, human as well as non-human animals such as dog, cow, horse, goat, sheep, ape, pig, rabbit, rat and mouse, etc. are mentioned. Among them, it is desirable to use one obtained from human for a use in research and development of a therapeutic agent for human beings.

The nucleic acid of the present invention can be obtained by utilizing information on a sequence disclosed in the present specification (SEQ ID NO: 1 of the below mentioned sequence listing). For example, primers and probes are designed based on the information of the disclosed nucleotide sequence, and using the same, it can be chosen and obtained from the DNA library by suitably combining PCR (polymerase chain reaction) method, colony hybridization method and plaque hybridization method.

For example, cDNA is synthesized from mRNA prepared from cells or tissues of mammals, and using this as a template, cDNA fragment is obtained by PCR method. Using the obtained cDNA as a probe, cDNA library is screened by colony hybridization method or plaque hybridization method to obtain a full-length cDNA. Also, genomic DNA can be isolated by screening genomic DNA library. Further, by screening DNA library of other mammals, homologous genes from different living species (orthologue) can be isolated.

DNA library such as cDNA library, genomic DNA library, etc. can be prepared according to a method described in, for example, "Molecular Cloning" (written by Sambrook, J., Fritsch, E. F. and Maniatis, T., published by Cold Spring Harbor Laboratory Press in 1989). Alternatively, commercially available libraries can be used if they are available.

By determining a nucleotide sequence of the obtained cDNA, a coding region which encodes the protein of a genetic product can be determined, to give an amino acid sequence of this protein.

The protein or polypeptide of the present invention can be produced by overexpression with a usual recombinant DNA technique. Also, it can be expressed and produced in a form of a fusion protein with other protein or a peptide.

The cell overexpressing the protein or the polypeptide of the present invention can be obtained, for example, as follows. A DNA coding the protein or the polypeptide of the present invention is inserted into a vector so that it is linked downstream of an appropriate promoter, thereby constructing an expression vector. Subsequently, the obtained expression vector is introduced in a host cell.

As an expression system (host-vector system), for example, expression systems such as bacteria, yeasts, insect cells and mammalian cells can be mentioned. Among these, for obtaining a functionally well preserved protein, insect cells (*Spodoptera frugiperda* SF9, SF21, etc.) and mammalian cells (monkey COS-7 cells, Chinese hamster CHO cells, human HeLa cells, etc.) are preferably used as a host.

As a promoter for expressing the protein or the polypeptide of the present invention, in case of the mammalian cell system, SV40 promoter, LTR promoter, elongation 1α promoter, etc., and in case of the insect cell system, polyhedrin promoter, etc., can be used.

As a vector to be used in these expression systems, in case of the mammalian cell system, retrovirus type vector, papilloma virus vector, vaccinia virus vector, SV40 type vector, etc. can be used, and in case of the insect cell system, baculovirus vector, etc. can be used.

As a DNA coding the protein or the polypeptide of the present invention, a cDNA corresponding to a naturally existing mRNA (for example, those comprising a nucleotide sequence shown by SEQ ID NO: 1) can be used, however, it is not limited to this. Alternatively, a DNA corresponding to an amino acid sequence of a desired protein is designed and used. In this case, 1 to 6 kinds of codons are known to code each of an amino acid, and codons to be used may be chosen randomly. However, for example, by considering a codon usage frequency of a host to be used for expression, a sequence with a higher expression efficiency can be designed. A DNA comprising the designed nucleotide sequence can be obtained by means of DNA chemical synthesis, fragmentation and linking of the above cDNA, partial modification of the nucleotide sequence, etc. Artificial and partial modification of the nucleotide sequence or an introduction of a mutation can be carried out by PCR method or site specific mutagenesis (Mark, et al., Proc. Natl. Acad. Sci. USA, Vol. 81, pp. 5662-5666, 1984), etc., using a primer comprising a synthetic oligonucleotide coding a desired modification.

The protein or the polypeptide of the present invention can be isolated and purified from a culture of the cells to which the expression vector is introduced, by suitably combining known purification methods (salting out by inorganic salts, fractional precipitation by an organic solvent, ion-exchange resin column chromatography, affinity column chromatography, gel filtration, etc.).

By overexpressing the protein or the polypeptide of the present invention, it is possible to enhance the functions or the activity of the protein or the polypeptide in the cells.

A nucleic acid (oligonucleotide or polynucleotide) which hybridizes with the nucleic acid of the present invention under a stringent condition or the complement thereof can be used as a probe for detecting the gene of the present invention. Also, they can be used, for example, as an anti-sense oligonucleotide, a ribozyme, or a decoy for modifying (e.g., inhibiting) an expression of a gene. As such a nucleic acid, for example, a nucleotide comprising, in principle, a partial sequence of successive 14 bases or more of a nucleic acid comprising the nucleotide sequence shown by SEQ ID NO: 1 (a sense strand or an antisense strand), or a complementary sequence thereof can be used.

Using the protein or the polypeptide of the present invention, or a protein or a peptide having an immunological equivalency thereto (a synthetic peptide containing a fragment or a partial sequence of a protein) as an antigen, an antibody which recognizes the protein or the polypeptide of the present invention can be obtained. Immunological equivalency means, for example, ability to cross-react with an antibody against the protein or the polypeptide of the present invention.

A polyclonal antibody can be prepared by an ordinary method of inoculating a host animal (for example, rat, rabbit, etc.) with an antigen, and collecting an immune serum. A monoclonal antibody can be prepared by an ordinary technique such as a hybridoma method. Further, a gene of a monoclonal antibody is modified to prepare a humanized monoclonal antibody.

Using the above-obtained antibody, an expression of the protein or the polypeptide of the present invention in a cell or a tissue can be detected by an ordinary immunochemical method (immunochemical assay, etc.). Also, by means of an affinity chromatography using an antibody, purification of the protein or the polypeptide of the present invention can be carried out. Further, using a neutralizing antibody, it is possible to modulate (e.g., to inhibit) the function or the activity of the protein or the polypeptide of the present invention.

The receptor protein or the polypeptide of the present invention has a function or an activity (a biological activity) as a receptor of eicosanoids (5-oxo-ETE, etc.). As such function or activity, there are mentioned, for example, the followings:
(i) Specific binding to a ligand,
(ii) Induction of intracellular signal transductions based on the stimulation by a ligand which acts as an agonist, and
(iii) Activation of G-protein [more specifically, $G_{i\alpha}$ (an $\alpha$ subunit of a G-protein belonging to $G_i$ subfamily, e.g., $G_{i\alpha 1}$) based on the stimulation by a ligand which acts as an agonist.

As the ligand which acts as an agonist includes, for example, eicosanoids such as 5-oxo-ETE, 5-HPETE, arachidonic acid, eicosa-5Z,8Z,11Z-trienoic acid, 5-HETrE, eicosa-5Z,8Z-dienoic acid, 5-HETE, ETI, etc. Among them, 5-oxo-ETE is particularly preferred.

The above-mentioned functions or activities of the receptor protein or the polypeptide of the present invention can be detected, for example, as follows.

Method for Detecting the Above Function or Activity (i):

The receptor protein or the polypeptide of the present invention (in the form of a membrane fraction containing the same, or in the form of cell expressing the same on the cell surface, etc.) is brought into contact with a ligand [eicosanoid, e.g., 5-oxo-ETE, 5-HPETE, arachidonic acid, eicosa-5Z,8Z,11Z-trienoic acid, 5-HETrE, eicosa-5Z,8Z-dienoic acid, 5-HETE, and ETI] to detect a specific binding between the both substances. For detecting such binding, for example, a labeled ligand (e.g., by RI labeling, fluorescence labeling, etc.) may be used. Specific binding can be detected by a conventional competitive assay, using an unlabeled ligand mixed with a labeled ligand.

Method for Detecting the Above Function or Activity (ii):

The cells expressing the receptor protein or the polypeptide of the present invention on the cell surface is brought into contact with a ligand [which acts as an agonist such as eicosanoid, e.g., 5-oxo-ETE, 5-HPETE, arachidonicacid, eicosa-5Z,8Z,11Z-trienoic acid, 5-HETrE, eicosa-5Z,8Z-dienoic acid, 5-HETE, and ETI, etc.,], to detect an induced intracellular signal transduction (change in $Ca^{2+}$ level, change in cAMP level, activation of phospholipase C, change in pH, change in $K^+$ level, etc.). As a control, a cell expressing the receptor protein or the polypeptide of the present invention in a lower level (or not expressing the same at all) are used, and when a level of the intracellular signal transduction is higher as compared to that of the control cell, the protein or the polypeptide is confirmed to have the function or activity (ii), depending on the level.

Specific method for detecting the intracellular signal transduction can be carried out, for example, according to the method described in the reference [Chen, et al., Analytical Biochemistry, Vol. 226, pp. 349-354, 1995 (change in $Ca^{2+}$ level and change in cAMP level); Graminski, et al., J. Biol. Chem., Vol. 268, pp. 5957-5964, 1993 (activation of phospholipase C); Sakurai, et al., Cell, Vol. 92, pp. 573-585, 1998 (change in $Ca^{2+}$ level); Hollopeter, et al., Nature, Vol. 409, pp. 202-207, 2001 (change in $K^+$ level); Tatemoto et al., Biochem. Biophys. Res. Commun. Vol. 251, pp. 471-476, 1998 (change in pH); Hinumaetal., Nature, Vol. 393, pp. 272-273, 1998 (arachidonic acid metabolite releasing); Japanese unexamined patent publication No. Hei9-268, etc.].

Method for Detecting the Above Function or Activity (iii):

From cells expressing a fusion protein of the receptor protein or the polypeptide of the present invention and $G_{i\alpha}$ (an a subunit of G-protein belonging to $G_i$ subfamily, e.g., $G_{i\alpha 1}$) on a cell membrane, a membrane fraction is prepared. The membrane fraction is brought into contact with a labeled GTP or an analogue thereof [e.g., a GTP analogue which is less metabolized, such as GTPγS (guanosine 5'-O-(3-thiotriphosphate)], in the presence or in the absence of a ligand (which acts as an agonist, such as eicosanoids, e.g., 5-oxo-ETE, 5-HPETE, arachidonic acid, eicosa-5Z,8Z,11Z-trienoic acid, 5-HETrE, eicosa-5Z,8Z-dienoic acid, 5-HETE, ETI, etc.]. Subsequently, binding of the labeled GTPs or its analogues to the membrane fraction is detected. If the binding level is higher in the presence of the ligand, as compared to the binding level in the absence of the ligand, the above-mentioned function or activity (iii) is confirmed depending on the level.

With respect to the $G_{i\alpha}$ (an a subunit of G-protein belonging to $G_i$ subfamily, e.g., $G_{i\alpha 1}$), or a gene thereof, an amino acid sequence or a nucleotide sequence have been already known [human $G_{i\alpha 1}$ (351Cys→Ile)/Bahia, et al., Biochemistry, Vol. 37, pp. 11555-11562, 1998: human $G_{i\alpha 1}$ Genbank/EMBL accession No. AF055013, PIR/SWISS-PROT accession No. P04898: etc.].

Based on the known information on the disclosed sequence, and using the same, a DNA encoding $G_{i\alpha}$ can be chosen and obtained from the DNA library by suitably combining PCR (polymerase chain reaction) method, colony hybridization method and plaque hybridization method. A DNA coding $G_{i\alpha}$ is linked downstream of DNA which encodes the receptor protein or the polypeptide of the present invention, so that it is inserted into a vector comprising an appropriate promoter, to construct an expression vector of the fused protein. And then, the obtained expression vector for the fused protein is introduced in a cell, to express a fused protein.

The receptor protein or the polypeptide of the present invention can be used for screening or identifying a ligand or an effector (an agonist or an antagonist) of the same.

A method for screening or identifying a ligand or an effector (an agonist or an antagonist) of the receptor protein or the polypeptide of the present invention can be carried out by the method which comprises the step of bringing the receptor protein or the polypeptide of the present invention (in a form of a membrane fraction containing the same, or in a form of a cell expressing the same on the cell surface, etc.) into contact with a test compound; and the step of detecting (1) a specific. binding of the receptor protein or the polypeptide with the test compound, (2) an intracellular signal transduction, and (3) an activation of G-protein ($G_{i\alpha}$), in the presence of the test compound.

More specifically, the method for screening or identifying a ligand, an agonist or an antagonist can be carried out as follows.

(A) Method for Screening or Identifying a Ligand

It can be carried out by (1) bringing the receptor protein or the polypeptide of the present invention (in a form of a membrane fraction containing the same, or in a form of a cell expressing the same on the cell surface, etc.) into contact with a test compound; (2) detecting a specific binding between the receptor protein or the polypeptide of the present invention and the test compound; and (3) analyzing if the test compound has an ability to bind to the receptor protein or the polypeptide of the present invention or not, or determining the strength of the ability.

The specific binding can be detected, for example, by an usual competitive assay, etc., where a known ligand which is labeled (e.g., by RI labeling, fluorescence labeling, etc.) is used, together with an unlabeled test compound.

It is highly possible that the test compound (ligand) having a specific binding ability is an effector (an agonist or an antagonist).

(B) Method for Screening or Identifying an Agonist

It can be carried out by (1) bringing the receptor protein or the polypeptide of the present invention (in a form of a membrane fraction containing the same, or in a form of a cell expressing the same on the cell surface, etc.) into contact with a test compound; (2) detecting in the presence of the test compound, an intracellular signal transduction or an activation of G-protein ($G_{i\alpha}$); and (3) analyzing if the test compound has an ability to transduce intracellular signals or an ability to activate G-protein or not based on the stimulation of the receptor protein or polypeptide, or determining the strength of the ability.

Detection of the intracellular signal transduction (change in $Ca^{2+}$ level, change in cAMP level, activation of phospholipase C, change in pH, change in $K^+$ level, etc.) or activation of G-protein ($G_{i\alpha}$) can be carried our in a similar manner as in the above-mentioned method.

(C) Method for Screening or Identifying an Antagnosit

It can be carried out by (1) bringing the receptor protein or the polypeptide of the present invention (in a form of a membrane fraction containing the same, or in a form of a cell expressing the same on the cell surface, etc.) into contact with a test compound and a ligand (which acts as an agonist, e.g., 5-oxo-ETE, etc.); (2) detecting the function or the activity of the receptor protein or the polypeptide of the present invention; and (3) analyzing if the test compound has an ability to inhibit the function or the activity of the receptor protein or the polypeptide of the present invention or not, or determining the strength of the ability.

As the ligand which acts as an agonist includes, for example, eicosanoids such as 5-oxo-ETE, 5-HPETE, arachidonic acid, eicosa-5Z,8Z,11Z-trienoic acid, 5-HETrE, eicosa-5Z,8Z-dienoic acid, 5-HETE, ETI, etc. Among them, 5-oxo-ETE is particularly preferred.

As the function or the activity of the receptor protein or the polypeptide of the present invention, there are mentioned the above-mentioned (i), (ii) or (iii), that is, (i) Specific binding to a ligand (e.g., 5-oxo-ETE),
(ii) Induction of intracellular signal transductions based on the stimulation by a ligand (which acts as an agonist, e.g., 5-oxo-ETE), and
(iii) Activation of G-protein based on the stimulation by a ligand (which acts as an agonist, e.g., 5-oxo-ETE).

Detection of the function or the activity can be carried out by, for example, a similar manner as in the above, except for adding the test compound, or not adding the test compound, in addition to the ligand (which acts as an agonist, e.g., 5-oxo-ETE).

In analyzing the ability of the test compound, an appropriate control should be used. As such control, detecting or testing in the absence of the test compound, detecting or testing using a cell not expressing the receptor protein of the present invention, or expressing the same in a lower level are mentioned. For a further accurate determination, a plural of such controls can be combined.

The compound which is selected or identified as an antagonist, by means of the above method, etc., can be brought into contact with the cells expressing the polypeptide of the present invention, to inhibit the function or the activity (the function or the activity as a receptor for the eicosanoids, e.g. 5-oxo-ETE) of the polypeptide in the cell.

The receptor protein or the polypeptide to be used for screening or identifying a ligand or an effector can be used in a form of a membrane fraction containing the same, or in a form of a cell expressing the same on the cell surface, etc.

As the cells expressing the receptor protein or the polypeptide on the cell surface, the cells overexpressing the receptor protein or the polypeptide, e.g., the cells in which a recombinant vector comprising a nucleic acid encoding the receptor protein or the polypeptide is introduced can be used.

As the host cell in which a recombinant vector is introduced, a cell capable of expressing the exogenous receptor protein on the cell surface, without impairing its function (mammalian cells, insect cells, etc.) can be used. Further, as the host cell, it is preferred to use the cells not expressing the target receptor protein or the polypeptide, or expressing the same only in a low level by themselves, before the recombinant vector is introduced.

The membrane fraction containing the receptor protein or the polypeptide can be prepared by homogenizing the cells expressing the receptor protein or the polypeptide, followed by a fractional method using centrifugal force, e.g., fractional centrifugation, density gradient centrifugation. For example, the cell homogenate is centrifuged at a low speed (about 500-3000 rpm) for a short period of time (normally about 1-10 minutes) to collect a supernatant, and the supernatant is further centrifuged at a high speed (about 15,000-30,000 rpm) for normally about 30 to 120 minutes. The thus-obtained sediment fraction is used as a membrane fraction.

About "5-oxo-ETE Receptor Antagonist":

Among the antagonists of the receptor protein of the present invention (the G-protein coupled receptor having an eicosanoid such as 5-oxo-ETE, etc. as a ligand), a compound having an ability to inhibit the intracellular signal transduction caused by a stimulation of the receptor by 5-oxo-ETE is hereinafter referred to as "5-oxo-ETE receptor antagonist".

The 5-oxo-ETE receptor antagonist may be either of a naturally existing compound or an artificially synthesized compound, as long as it has such an ability.

Specific examples of the 5-oxo-ETE receptor antagonist include a polyunsaturated fatty acid, e.g., docosahexaenoic acid (DHA), eicosapentaenoic acid (EPA), dihomo-γ-linolenic acid, and eicosa-11Z,14z,17Z-trienoic acid, etc.

The 5-oxo-ETE receptor antagonist are not limited to the above specific examples. Any compound which acts as an antagonist can be suitably selected and identified from the compounds widely existing in the nature, and the newly synthesized compounds.

These antagonists can be used in a free form or in other pharmaceutically acceptable form. When it is a polyunsaturated fatty acid compound, it is preferably used in a free form. Selection and identification of the antagonist can be carried by the above-mentioned method, using 5-oxo-ETE as a ligand (agonist), and specifically, by a method similar to that described in the following Example 4 and Example 6.

As mentioned above, the receptor of the present invention mediates migrations of eosinophils and neutrophils induced by 5-oxo-ETE.

Therefore, by administration of the antagonist of the receptor protein of the present invention (specifically the 5-oxo-ETE receptor antagonist), it is possible to inhibit the migrations of eosinophils and/or neutrophils.

Further, a pharmaceutical composition comprising the 5-oxo-ETE receptor antagonist as an effective ingredient, and a method comprising administering to a patent an effective amount of the 5-oxo-ETE receptor antagonist can be applied for treatment and prophylaxis of diseases whose pathological states are expected to be alleviated by inhibiting migrations of eosinophils or neutrophils.

As the disease whose pathological states are expected to be alleviated by inhibiting migrations of eosinophils or neutrophils, there are mentioned, for example, diseases in which migrations of eosinophils and/or neutrophils are involved in onset and progress of the pathological state, e.g., immunological diseases such as allergy (asthma, etc.), inflammation (arthritis, dermatitis, etc.).

Further, the 5-oxo-ETE receptor antagonist can induce apoptosis in cancer cells. The apoptosis is one kind of a genetically programmed cell death, and it is normally observed as natural phenomena of normal cells. It is expected that one of the reason the cancer develops is that the cells are not led to apoptosis (Annu. Rev. Immunol., 17, pp. 221-253, 1999).

Therefore, by administering the 5-oxo-ETE receptor antagonist, it is possible to induce apoptosis in cancer cells, and a pharmaceutical composition comprising the 5-oxo-ETE receptor antagonist as an effective ingredient, and a method comprising a step of administering to a patient an effective amount of the 5-oxo-ETE receptor antagonist can be applied to treatment and prophylaxis of cancer.

Specific examples of such cancer include prostate cancer, breast cancer, lung cancer, pancreas cancer, and mesothelioma, and it is preferably applied to prostate cancer.

An action of the 5-oxo-ETE receptor antagonist to inhibit the migration of eosinophils and/or neutrophils can be confirmed in a similar manner as described in Example 6 and Example 7. Further, the action of the 5-oxo-ETE receptor antagonist to induce apoptosis can be confirmed in a similar manner as described in Example 8.

In the pharmaceutical composition or the method for treatment of the present invention, an administration route is not particularly limited, and conventional oral or parenteral route (intravenous, intramuscular, transdermal, subcutaneous, transnasal, or other transmucosal administration route, enteral route, etc.) can be applied.

Further, the 5-oxo-ETE receptor antagonist being the effective ingredient, is appropriately formulated into conventional preparations (tablets, granules, capsules, powders, inhalants, etc.) with an inert carrier depending on the administration route and used.

For example, the antagonist can be mixed with a conventional carrier which is acceptable for general pharmaceuticals, such as an excipient or a diluent, e.g., a binder, a disintegrant, an extender, a filler, and a lubricant, etc. to obtain a pharmaceutical composition. Such composition can be used or sold as a pharmaceutical.

In addition, a dose amount of the active ingredient may be optionally chosen, depending on potencies or properties of the antagonist as an active ingredient, within a range of a sufficient effective amount for exhibiting a drug efficacy. The dose may vary depending on an administration route, age, bodyweight, and condition of a patient, and it is suitably selected from a generally used dose range, for example, a range of 0.01 to 300 mg/kg per day, in case of an oral administration, and 0.01 to 50 mg/kg per day in case of a parenteral administration.

The pharmaceutical composition or the therapeutic method of the present invention exhibits its drug efficacy based on an antagonistic action of the antagonist as an effective ingredient (an antagonistic action against the receptor of the present invention).

Therefore, pharmaceuticals and therapeutic method expressing drug efficacy, based on the actions other than the above are not included in the scope of the present invention.

Further, the composition of the present invention may be used solely for treating the above-mentioned diseases, as stated above, however, this use does not exclude any combination use of other pharmaceuticals which are conventionally employed.

Hereinafter, the present invention will be explained in more detail by referring to the following Examples but these Examples do not intend to limit the present invention.

In the following Examples, unless otherwise specified, each operation was carried out according to a method described in "Molecular Cloning" (written by Sambrook, J., Fritsch, E. F. and Maniatis, T., published by Cold Spring Harbor Laboratory Press in 1989). Alternatively, in case of using commercially available reagents or kits, it was carried out according to protocols attached to the commercial products.

EXAMPLES

Example 1

Isolation of Human TG1019

(1) Amino acid sequences of 62 G-protein coupled receptors having a peptide as a ligand were aligned, to determine a highly conserved amino acid sequence (SEQ ID NO:3) among these G-protein coupled receptors. Using this sequence (SEQ ID NO:3) as a query sequence, search was carried out in the High-Throughput Genomic Sequences database of NCBI (National Center for Biotechnology Information), using tblastn (Altschul S F, et al., J. Mol. Biol., Vol. 215, pp. 403-410, 1990), as a homology search method. As a result, a sequence having a high homology (SEQ ID NO:4) was found in the clone AC013396.3. Using the sequence of AC013396.3, an open reading frame (SEQ ID NO:5) comprising this sequence (SEQ ID NO:4) was deduced. With respect to an amino acid sequence of a polypeptide encoded by the open reading frame (SEQ ID NO:5), prediction of transmembrane domains was carried out using HMMTOP (system for predicting Transmembrane topology and transmembrane helices) (Tusnady G E, et al., J. Mol. Biol., Vol. 283, pp. 489-506, 1998), and homology comparison with the known G-protein coupled receptor was carried out. As a result, the nucleotide sequence shown by SEQ ID NO:5 was expected to encode an entire region of a novel G-protein coupled receptor.

(2) Based on the nucleotide sequence of AC013396.3 of the above (1), a primer was designed, and a DNA comprising the sequence of SEQ ID NO:5 was obtained using PCR.

Using a human cDNA library (trade name: Human Universal QUICK-Clone cDNA; available from Clonetech), the primary PCR was conducted. In the procedure, as the sense primer was used a synthetic oligonucleotide comprising a nucleotide sequence shown by SEQ ID NO:6 (a primer corresponding to a region comprising the $97735^{th}$-$97760^{th}$ bases of the AC013396.3), and as the antisense primer was used a synthetic oligonucleotide comprising a nucleotide sequence shown by SEQ ID NO:7 (a primer corresponding to a region comprising the $96299^{th}$-$96324^{th}$ bases of the AC013396.3). A PCR reaction mixture (25 µl) containing these primers and a template cDNA [composition: 1 µl of a template cDNA (trade name: Human Universal QUICK-Clone cDNA, Clonetech), 18.5 µl of sterilized water, 2.5 µl of PCR buffer (Advantage 2 PCR Buffer, Clonetech), 0.5 µl of a deoxynucleotide solution (dATP, dCTP, dGTP, and dTTP, 10 mM each), 0.5 µl of polymerase solution (Advantage 2 Polymerase Mix, Clonetech), 1.0 µl of sense primer (10 µM), and 1.0 µl of antisense primer (10 µM)] was prepared. And then, PCR reaction was carried out [Conditions: 94° C. for 30 sec., (94° C. for 30 sec.→64° C. for 30 sec. →72° C. for 2.5 min.)×30 times, 72° C. for 2.5 min.]. Subsequently, 1 µl of the above-obtained PCR reaction mixture was used as a template, the secondary PCR was carried out. In the reaction, a composition of the PCR reaction mixture and a reaction condition were the same as the above. The obtained PCR products were subjected to an agarose gel electrophoresis and a band was cut out to isolate and purify a cDNA fragment (about 1500 bp) containing the sequence of SEQ ID NO:5. This fragment was linked to a vector plasmid (PGEM-T Easy, available from Promega), and the obtained plasmid was used to determine a nucleotide sequence of the cDNA fragment. As a result, a nucleotide sequence shown by SEQ ID NO:1 (1462 bp) was confirmed.

In the nucleotide sequence shown by SEQ ID NO:1, there was identified one open reading frame. An amino acid sequence (423 amino acid residues) of a protein encoded by this (referred to as TG1019) was as shown by SEQ ID NO:2. With respect to SEQ ID NO:2, prediction of the transmembrane domain by HMMTOP and a homology comparison with the known G-protein coupled receptors were carried out, and as result, it was expected that TG1019 protein was a novel G-protein coupled receptor, and that the above-obtained cDNA (1462 bp) was a cDNA covering an entire coding region of a gene (referred to as TG1019 gene) of the TG1019 protein. FIG. 2 shows the nucleotide sequence and the amino acid sequence, together with a transmembrane domains (underlined).

Comparison was made between a DNA nucleotide sequence of SEQ ID NO:1 and human genome DNA sequences registered in Genbank (Genbank Accession No. AC013396 (ver 3)), and differences were confirmed in 4 bases between them, which were $487^{th}$ base (G$\leftrightarrows$A), the $771^{st}$ base (G$\leftrightarrows$A), the $1022^{nd}$ base (C$\leftrightarrows$A), and the $1038^{th}$ base (G$\leftrightarrows$A) in SEQ ID NO:1.

In accordance with the differences in bases, there also arose differences in 3 amino acid residues in an amino acid sequence of the polypeptide encoded by the DNA, which were the $150^{th}$ residue (Gly$\leftrightarrows$Asp), the $245^{th}$ residue (Glu$\leftrightarrows$Lys), and the $334^{th}$ residue (Ala$\leftrightarrows$Thr) in SEQ ID NO:2.

Therefore, PCR was carried out (independently twice), using as a template a human cDNA library (trade name: Marathon Ready cDNA library, fetal human spleen; available from Clonetech), to obtain Apa I fragments containing bases for which the above discrepancies were observed, and the nucleotide sequences were analyzed for several clones.

As a result, it is thought that the difference in the $1022^{nd}$ base (C$\leftrightarrows$A) in SEQ ID NO:1 was resulted from nucleotide polymorphism, and derived from naturally occurring allelic variants. This difference in nucleotide sequence will not cause any difference in amino acid sequence of the polypeptide encoded thereby.

On the contrary, the differences in the $487^{th}$ base (G$\leftrightarrows$A), the $771^{st}$ base (G$\leftrightarrows$A), and the $1038^{th}$ base (G$\leftrightarrows$A) in SEQ ID NO:1 are thought to be due to a PCR error, and for these bases, it is expected that the sequence of Genbank Accession No. AC013396 (ver3) was correct.

Thus, in the nucleotide sequence in which any PCR errors, etc. are corrected, the $487^{thb}$ base, the $771^{st}$ base, the $1022^{nd}$ base and the $1038^{th}$ base in SEQ ID NO:1 are expected to be "A" (Adenine), and in an amino acid sequence of a polypeptide encoded by the revised nucleotide sequence, it is expected that the $150^{th}$, the $245^{th}$, and the $334^{th}$ residues in SEQ ID NO:2 are respectively Asp, Lys and Thr.

A nucleotide sequence after the PCR errors have been corrected is shown by SEQ ID NO:20 in the sequence listing mentioned below, and an amino acid sequence of a polypeptide encoded thereby is shown by SEQ ID NO:21, respectively.

Example 2

Expression Pattern of TG1019 Gene

Expression patterns of the TG1019 gene in various human tissues and cells were analyzed by dot blotting analysis. Dot blotting was carried out using mRNAs derived from human tissues and human cultured cells (dotted on a nylon membrane) (Multiple Tissue Expression Array, available from Clonetech), and RI-labeled probes. On the membrane, mRNAs [poly(A)RNA] derived from various human tissues and human cultured cells mentioned in FIG. 3 were dotted (adsorbed and fixed).

As the RI-labeled probes, those prepared as follows were used. Specifically, the plasmid containing the cDNA fragment obtained in Example 1 (2) mentioned above was digested by a restriction enzyme Not I, and then, an about 1500 bp of the DNA fragment (a cDNA fragment covering an entire coding region of the TG1019 gene) was purified and obtained by an agarose gel electrophoresis. Using this cDNA as a template, labeling was carried out using a labeling kit (Prime-a-Gene Labeling system, available from Promega) containing random primers (random hexadeoxyribonucleotides), a mixed nucleotide solution (dATP, dGTP and dTTP) and DNA polymerase I (Large (Klenow) Fragment) and [$\alpha$-$^{32}$P] dCTP, then, the resultant was purified by gel filtration, to prepare RI-labeled probe.

Hybridization in dot blotting was carried out as follows.

A membrane on which mRNAs were fixed was preincubated in a solution I [prepared by treating Salmon Testes DNA (160 μl, 9.4 μg/μl: Sigma) at 97° C. for 5 minutes, cooling the same on ice, and adding ExpressHyb hybridization Solution (15 ml: Clonetech) kept at 60° C.] at 68° C. for 30 minutes.

Subsequently, this membrane was placed in a hybridization solution containing the labeled probes [prepared by mixing the above-obtained RI-labeled probes (20 μl), human COT-1 DNA (30 μl, 1 μg/μl: Roche), Salmon Testes DNA (16 μl, 9.4 μg/μl: Sigma), 20×SSC (50 μl, 3M sodium chloride, 300 mM sodium citrate, pH7.0), and nuclease-free H$_2$O (84 μl: Promega), to prepare 200 μl of solution, treating the same at 97° C. for 5 minutes, incubating the same at 68° C. for 30 minutes, and further adding thereto 5 ml of the above solution I] and hybridization was carried out at 65° C. for 12 hours. Then the membrane was pre-washed five times with 2×SSC (300 mM sodium chloride, 30 mM sodium citrate, pH7.0) containing 1% SDS at 65° C. for 20 minutes, and then, washed two times with 0.1×SSC (15 mM sodium chloride, 1.5 mM sodium citrate, pH7.0) containing 0.5% SDS at 55° C. for 20 minutes.

Using an image analyzer (Bio-imaging Analysis System 2000, available from Fujifilm), signals from hybridization were analyzed. As a result, signals were detected for mRNAs of almost all tissues, among the tissues subjected to the test (see FIG. 3). Among the tissues where the signals were detected, relatively strong signals were detected in liver, kidney, peripheral leukocyte and spleen. From these results, it is expected that TG1019 gene is expressed in many tissues, and among them, it is expressed in relatively higher level in liver, kidney, peripheral leukocyte and spleen.

Example 3

Identification of a Ligand of TG1019 Protein (G-protein Coupled Receptor)

As stated in Example 1, it is concluded that TG1019 protein is a G-protein coupled receptor. Therefore, using a membrane fraction containing fused protein of TG1019 and G-protein, a ligand is identified as follows, according to a method for detecting a ligand-dependent binding with GTPγS (guanosine 5'-O-(3-thiotriphosphate)) [Wenzel-Seifert, et al., Mol. Pharmacom., Vol. 58, pp. 954-966, 2000; Bahia, et al., Biochemistry, Vol. 37, pp. 11555-11562, 1998].

(1) Preparation of a Plasmid for Expressing a Fusion Protein

Figure 1:
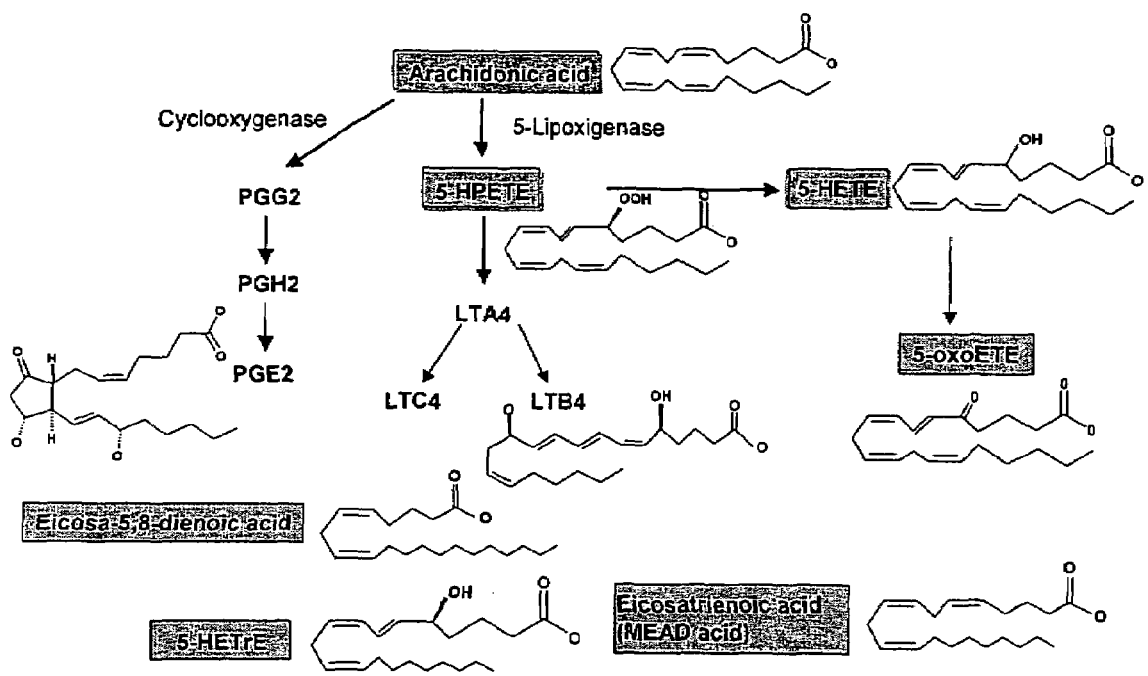
FIG. 1 shows a biosynthetic pathway of eicosanoids such as 5-oxo-ETE, etc.
Figure 4:
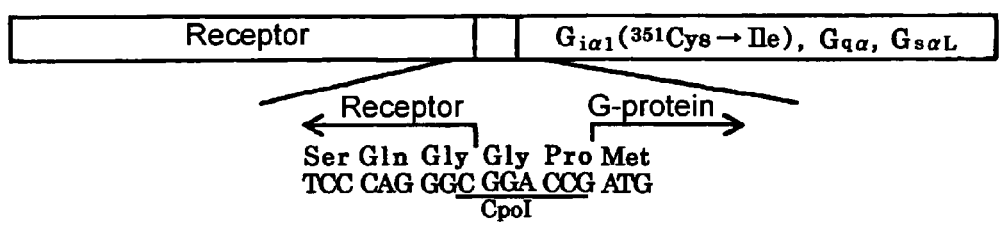
FIG. 4 shows a schematic diagram of structure of a fused protein of TG1019 protein and various G-proteins.
Figure 5A:
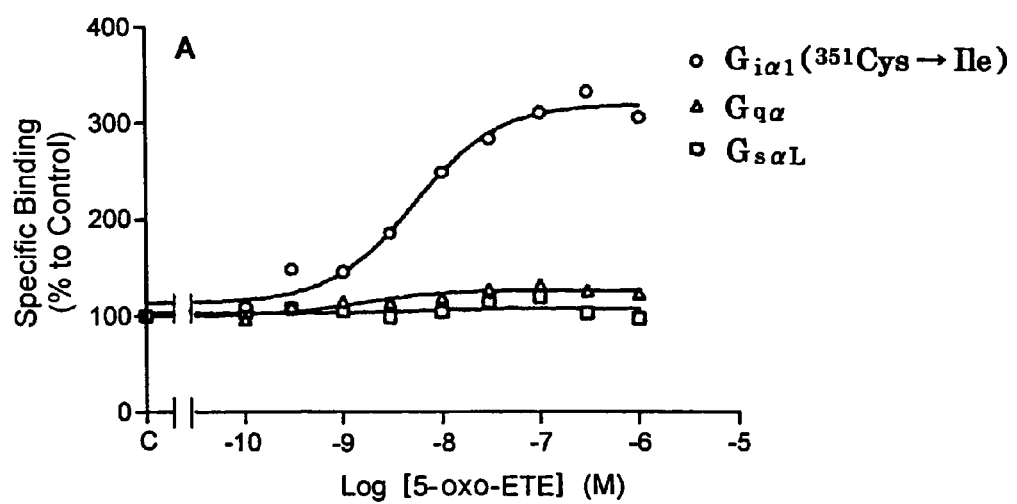
FIG. 5A shows an effect of respective test compounds on a specific binding amount of a membrane fraction containing a fused protein of TG1019 protein and various G-proteins, with GTPγS, when 5-oxo-ETE is used as a test compound.
Figure 5B:
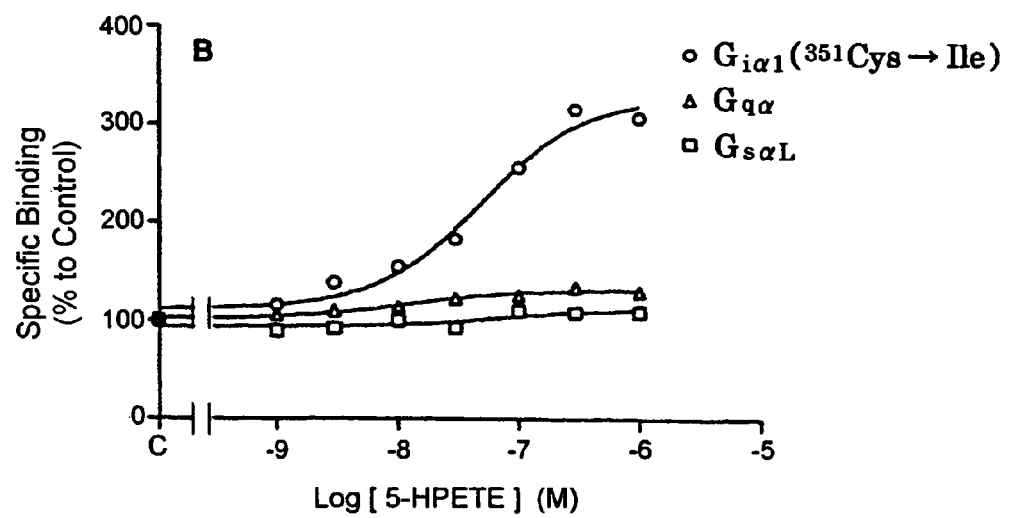
FIG. 5B shows an effect of respective test compounds on a specific binding amount of a membrane fraction containing a fused protein of TG1019 protein and various G-proteins, with GTPγS, when 5-hydroperoxyeicosa-6E,8Z,11Z,14Z-tetraenoic acid (5-HPETE) is used as a test compound.
Figure 5C:
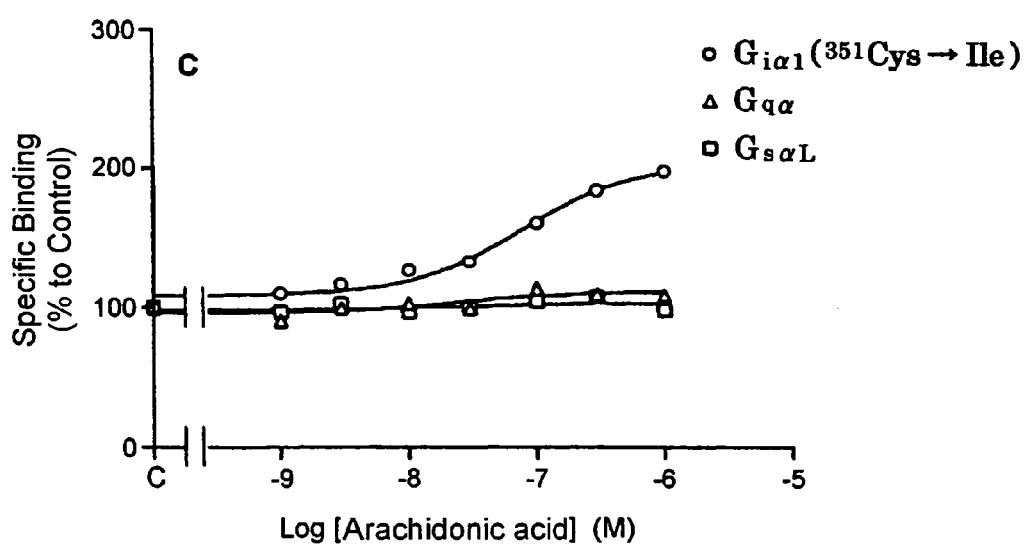
FIG. 5C shows an effect of respective test compounds on a specific binding amount of a membrane fraction containing a fused protein of TG1019 protein and various G-proteins, with GTPγS, when arachidonic acid is used as a test compound.
Figure 5D:
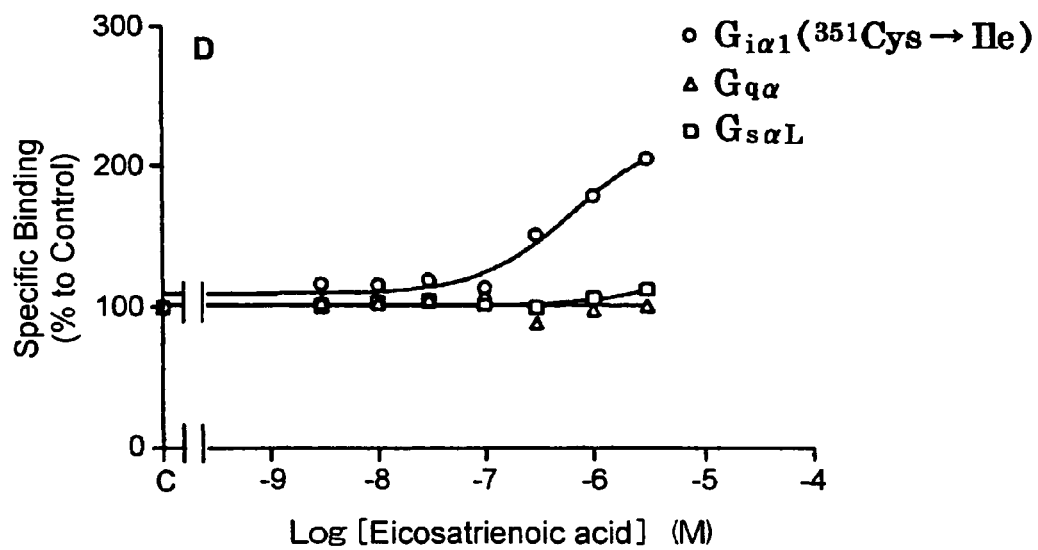
FIG. 5D shows an effect of respective test compounds on a specific binding amount of a membrane fraction containing a fused protein of TG1019 protein and various G-proteins, with GTPγS, when eicosa-5Z,8Z,11Z-trienoic acid is used as a test compound.
Figure 5E:
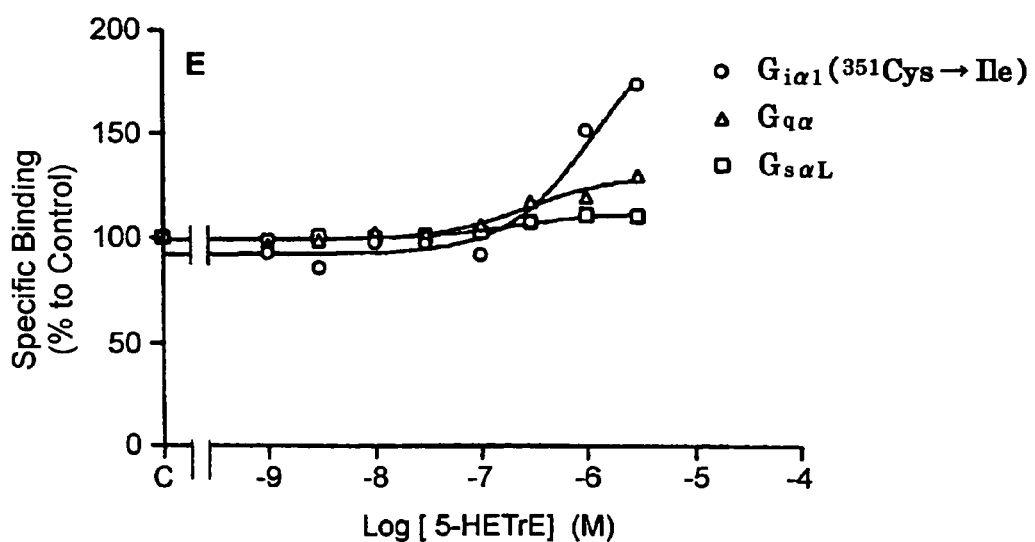
FIG. 5E shows an effect of respective test compounds on a specific binding amount of a membrane fraction containing a fused protein of TG1019 protein and various G-proteins, with GTPγS, when 5-hydroxyeicosa-6E,8Z,11Z-trienoic acid (5-HETrE) is used as a test compound.
Figure 5F:
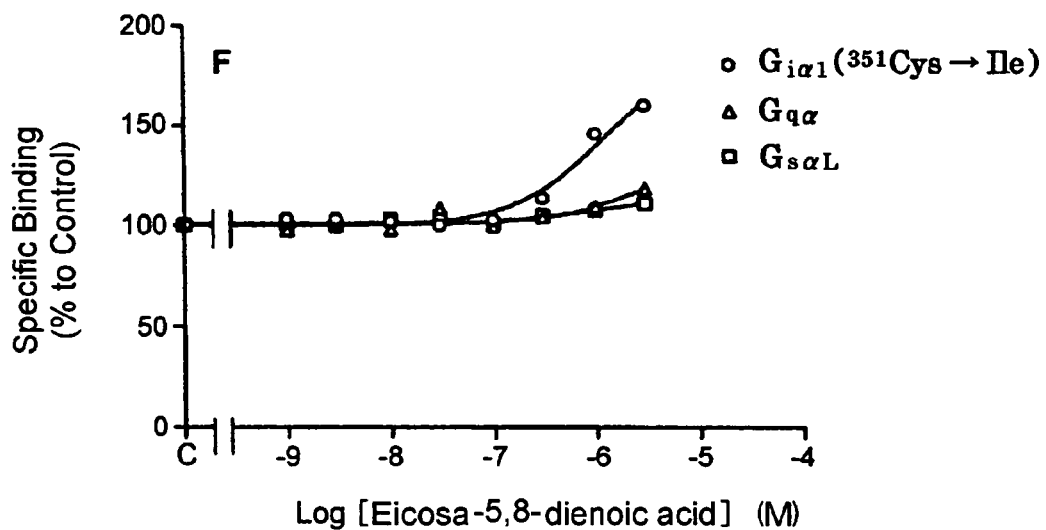
FIG. 5F shows an effect of respective test compounds on a specific binding amount of a membrane fraction containing a fused protein of TG1019 protein and various G-proteins, with GTPγS, when eicosa-5Z,8Z-dienoic acid is used as a test compound.
Figure 5G:
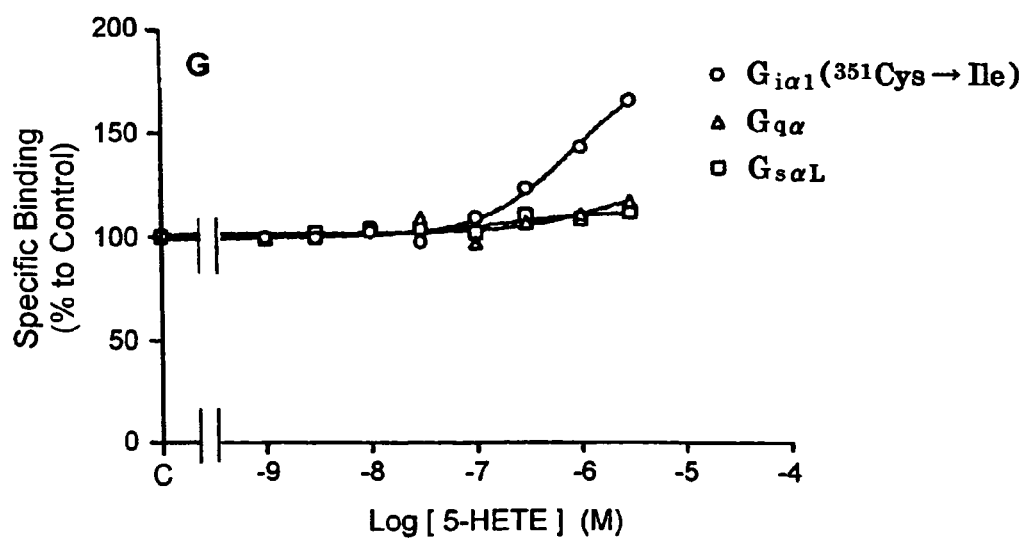
FIG. 5G shows an effect of respective test compounds on a specific binding amount of a membrane fraction containing a fused protein of TG1019 protein and various G-proteins, with GTPγS, when 5-HETE is used as a test compound.
Figure 5H:
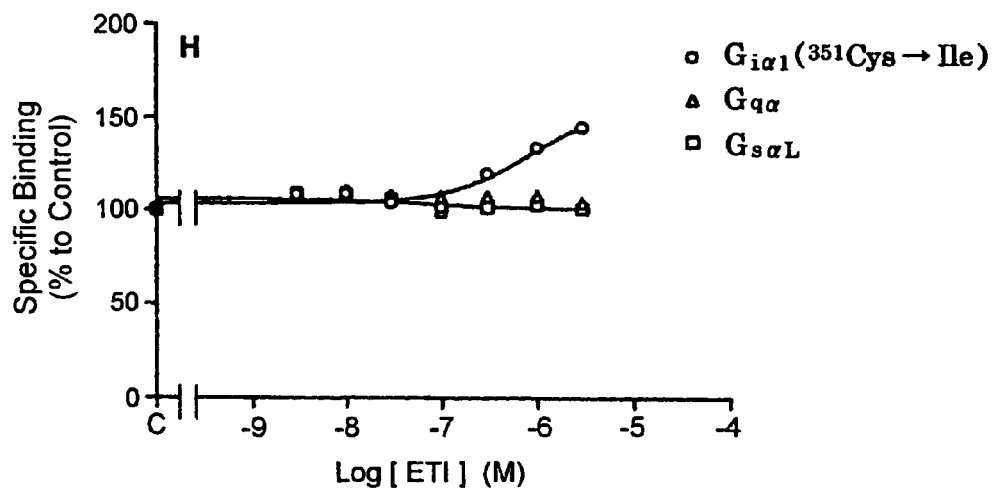
FIG. 5H shows an effect of respective test compounds on a specific binding amount of a membrane fraction containing a fused protein of TG1019 protein and various G-proteins, with GTPγS, when 5,8,11-eicosatriynoic acid (ETI) is used as a test compound.

As described in the following (A) to (D), a plasmid for expressing a fusion protein of TG1019 protein and G-protein [$G_{i\alpha 1}$ (351Cys→Ile), $G_{q\alpha}$, or $G_{s\alpha L}$] is prepared. The schematic diagram of a fused protein is shown in FIG. 4. $G_{i\alpha 1}$ (351Cys→Ile) means a variant form of $G_{i\alpha 1}$ protein in which the $351^{st}$ cysteine residue is replaced with isoleucine residue.

(A) Preparation of cDNA of TG1019 Gene

PCR was carried out using as a template, the plasmid containing the cDNA of TG1019 gene (containing an entire coding region) obtained in Example 1 (2) mentioned above.

In this procedure, as a sense primer (primer TG1019-1) and an anti-sense primer (primer TG1019-2), synthetic oligonucleotides comprising nucleotide sequences shown by SEQ ID NO:8 and SEQ ID NO:9 were used, respectively.

These primers were designed based on the nucleotide sequence of cDNA of TG1019 gene (SEQ ID NO:1), and they were designed so that a DNA fragment is obtained as a PCR product, which comprises a cDNA encoding an entire region of TG1019 protein (except for a stop codon), and has restriction enzyme recognition sites attached to the both termini (Bgl II site at N-terminus, and Cpo I site and Hind III site at C-terminus).

The thus obtained PCR product was linked to a vector plasmid (vector system for cloning PCR products) (pGEM-T Easy Vector, available from Promega), and the resultant plasmid was digested by restriction enzyme Not I and Cpo I, to collect the resulting DNA fragment of about 1,300 bp.

(B) Preparation of Plasmid for Expressing a Fusion Protein with G-protein ($G_{i\alpha 1}$ (351Cys→Ile))

PCR was carried out using as a template, a cDNA derived from human brain (Marathon-Ready cDNA Brain, available from Clonetech). In this procedure, as a sense primer (primer $G_{i\alpha 1}$-1) and an anti-sense primer (primer $G_{i\alpha 1}$-2), synthetic oligonucleotides comprising nucleotide sequences shown by SEQ ID NO:10 and SEQ ID NO:11 were used, respectively.

These primers were designed based on the known nucleotide sequence of cDNA encoding $G_{i\alpha 1}$ protein (Genbank/EMBL Accession No. AF055013), and they were designed so that a cDNA encoding an entire region of $G_{i\alpha 1}$ protein is obtained as a PCR product.

Subsequently, using the PCR product as a template, the secondary PCR was carried out. In this procedure, as a sense primer (primer $G_{i\alpha 1}$-3) and an anti-sense primer (primer $G_{i\alpha 1}$-4), synthetic oligonucleotides comprising nucleotide sequences shown by SEQ ID NO:12 and SEQ ID NO:13 were used, respectively.

These primers were designed so that a DNA fragment is obtained as a PCR product, which comprises a cDNA encoding an entire region of $G_{i\alpha 1}$ (351Cys→Ile) (a variant form of $G_{i\alpha 1}$ protein in which the $351^{st}$ cysteine residue is replaced with isoleucine residue), and has restriction enzyme recognition sites attached to the both termini (Cpo I site and BamHI site).

The thus obtained PCR product was linked to a vector plasmid (pGEM-T Easy Vector, available from Promega). This plasmid was digested by restriction enzyme NotI and BamHI, and the resultant DNA fragments of about 1100 bp were inserted into a NotI/BamHI site of a baculovirus vector plasmid pVL1392 (available from Pharmingen) to obtain a plasmid pVL1392/$G_{i\alpha 1}$ (351Cys→Ile).

To the NotI/CpoI site in this plasmid was inserted the DNA fragment obtained in (A) above, to prepare a fusion protein expression plasmid pVL1392/TG1019-$G_{i\alpha 1}$ (351Cys→Ile)

(C) Preparation of Plasmid for Expressing a Fusion Protein with G-protein ($G_{q\alpha}$)

PCR was carried out using as a template, a cDNA derived from human prostate (Marathon-Ready cDNA Prostate, available from Clonetech). In this procedure, as a sense primer (primer $G_{q\alpha}$-1) and an anti-sense primer (primer $G_{q\alpha}$-2), synthetic oligonucleotides comprising nucleotide sequences shown by SEQ ID NO:14 and SEQ ID NO:15 were used, respectively. These primers were designed based on the known nucleotide sequence of cDNA encoding $G_{q\alpha}$ (protein (Genbank/EMBL Accession No. U43083), and they were designed so that a cDNA encoding an entire region of $G_{q\alpha}$ protein is obtained as a PCR product.

Subsequently, using the PCR product as a template, the secondary PCR was carried out. In this procedure, as a sense primer (primer $G_{q\alpha}$-3) and an anti-sense primer (primer $G_{q\alpha}$-4), synthetic oligonucleotides comprising nucleotide sequences shown by SEQ ID NO:16 and SEQ ID NO:17 were used, respectively. These primers were designed so that a DNA fragment is obtained as a PCR product, which comprises a cDNA encoding an entire region of $G_{q\alpha}$, and has restriction enzyme recognition sites attached to the both termini (Cpo I site and BamHI site).

The thus obtained PCR product was linked to a vector plasmid (pGEM-T Easy Vector, available from Promega). The obtained plasmid was digested by restriction enzyme NotI and BamHI, and the resultant DNA fragments of about 1100 bp were inserted into a NotI/BamHI site of a baculovirus vector plasmid pVL1392 to obtain a plasmid pVL1392/$G_{q\alpha}$.

To the NotI/CpoI site in this plasmid was inserted the DNA fragment obtained in (A) above, to prepare a fusion protein expression plasmid pVL1392/TG1019-$G_{q\alpha}$.

(D) Preparation of Plasmid for Expressing a Fusion Protein with G-protein ($G_{s\alpha L}$)

PCR was carried out using as a template, a cDNA derived from human bone marrow (Marathon-Ready cDNA Bone marrow, available from Clonetech). In this procedure, as a sense primer (primer $G_{s\alpha L}$-1) and an anti-sense primer (primer $G_{s\alpha L}$-2), synthetic oligonucleotides comprising nucleotide sequences shown by SEQ ID NO:18 and SEQ ID NO:19 were used, respectively.

These primers were designed based on the known nucleotide sequence of cDNA encoding $G_{s\alpha L}$ protein (Genbank/EMBL Accession No. X04408), and they were designed so that a DNA fragment is obtained as a PCR product, which comprises a cDNA encoding an entire region of $G_{s\alpha L}$, and has restriction enzyme recognition sites attached to the both termini (Cpo I site and XbaI site).

The thus obtained PCR product was linked to a vector plasmid (pGEM-T Easy Vector, available from Promega). The obtained plasmid was digested by restriction enzyme NotI and XbaI, and the resultant DNA fragments of about 1200 bp were inserted into a NotI/XbaI site of a baculovirus vector plasmid pVL1392 (available from Pharmingen) to obtain a plasmid pVL1392/$G_{s\alpha L}$.

To the NotI/CpoI site in this plasmid was inserted the DNA fragment obtained in (A) above, to prepare a fusion protein expression plasmid pVL1392/TG1019-$G_{s\alpha L}$.

(2) Preparation of a Membrane Fraction Containing a Fusion Protein

Three kinds of the expression plasmids obtained in the above (1)(B) to (1)(D) are plasmids expressing fusion proteins having a structure as shown in FIG. 4 (schematic diagram) in which TG1019 protein (full length) and G-protein [$G_{i\alpha1}$ (351Cys→Ile), $G_{q\alpha}$ or $G_{s\alpha L}$] are linked via a linker sequence (-Gly-Pro-) added to the C-terminus of TG1019 protein.

These fusion protein expression plasmids pVL1392/TG1019-$G_{i\alpha1}$ (351Cys→Ile), pVL1392/TG1019-$G_{q\alpha}$, and pVL1392/TG1019-$G_{s\alpha L}$ were expressed in insect cells as follows to prepare a membrane fraction containing the fusion protein.

First, insect cells Sf9 (*Spodoptera frugiperda* SF9) (available from Pharmingen) were incubated to about 60% confluence in a 3 cm Petri dish coated with collagen, in 1.5 ml of culture medium [Grace's Insect Cell Culture Medium (pH6.2:available from Lifetech Oriental) containing 10% fetal bovine serum, 0.1 mg/ml streptomycin and 100 U/ml penicillin] at 27° C. for 15 minutes.

After the culture medium was removed and 375 µl of a transfection buffer (Transfection Buffer A, available from Pharmingen) was added thereto, 400 µl of DNA solution which had been prepared beforehand [prepared by mixing 1 µg of a fusion protein expression plasmid and 0.125 µg of Linearized BaculoGold Baculovirus DNA (available from Pharmingen) in 25 µl of sterilized water, incubating the mixture at 25° C. for 15 minutes, and adding thereto 375 µl of Transfection Buffer B (available from Pharmingen)] was added dropwise thereto.

The resultant was cultured at 27° C. for 4 hours, the culture solution was removed, 1.2 ml of a culture medium was added, and it was incubated at 27° C. for 5 days. The obtained culture solution was centrifuged (1,000×g, 5 minutes), to collect a supernatant as Virus solution I.

Sf9 cells were inoculated onto a 3 cm Petri dish coated with collagen to about 30% confluence, and added thereto were Virus solution I (100 µl) obtained above and 1.2 ml of a culture medium, and the mixture was cultured at 27° C. for 4 days. The obtained culture solution was centrifuged (1,000×g, 5minutes), to collect a supernatant as Virus solution II.

Sf9 cells were inoculated onto a 10 cm Petri dish coated with collagen to about 70% confluence, and added thereto were Virus solution II (500 µl) obtained above and 12 ml of a culture medium, and the mixture was cultured at 27° C. for 4 days. The obtained culture solution was centrifuged (1,000× g, 5 minutes), to collect a supernatant as Virus solution III.

Sf9 cells were inoculated onto a 10 cm Petri dish coated with collagen to about 70% confluence, and added thereto were Virus solution III (100 µl) obtained above and 12 ml of a culture medium, and the mixture was cultured at 27° C. for 4 days. The obtained cells were washed with a cooled PBS (Phosphate buffered saline, pH 7.4), and suspended in 3.6 ml of a cooled solution buffer [20 mM Tris-HCl, pH 7.5, 1 mM EDTA, 0.2 mM phenylmethylsulfonyl fluoride, 10 µg/ml pepstatin, 10 µg/ml leupeptin, and 2 µg/ml aprotinin], and the cells were homogenized by means of a Teflon homogenizer. This cell homogenate was centrifuged (600×g, 10 minutes), and the resultant supernatant was further centrifuged (50,000×g, 20 minutes). The obtained sediments were suspended in 450 µl of a cooled reaction buffer [20 mM Tris-HCl, pH 7.5, 50 mM sodium chloride, 10 mM magnesium chloride] by means of a Teflon homogenizer, to prepare a membrane fraction containing a fusion protein.

(3) Binding Analysis of the Membrane Fraction Containing a Fusion Protein and GTPγS The membrane fraction (450 µl) obtained above (2) was suspended in a reaction buffer (7.54 ml), and added thereto was GDP (10 mM, 10 µl). To 160 µl of this solution was added 20 µl of a test compound. After incubating the mixture at 30° C. for 10 minutes, 20 µl of [$^{35}$S] GTPγS (5 nM, 5 nCi/µl: available from Amersham Pharmacia Biotech) was added to start reaction. After incubating the mixture at 30° C. for one hour, the reaction was terminated by filtration through a glass filter (UniFilter-96GF/B, available from Packard). The filter was washed with 200 µl of a cooled reaction buffer for 3 times, and an amount of the [$^{35}$S] GTPγS (a binding amount to the membrane fraction) on the filter was measured by liquid scintillation counting. From the thus measured [$^{35}$S] GTPγS binding amount was subtracted a nonspecific binding amount (a binding amount measured in the presence of 10 µM GTPγS), to obtain a specific binding amount of [$^{35}$S] GTPγS.

About 370 kinds of nucleic acids, amino acids, peptide-related compounds, tissue extracts, and lipid-related compounds were tested as test compounds. As a result (see FIG. 5), when a membrane fraction containing a fusion protein of TG1019 protein and $G_{i\alpha1}$ (351Cys→Ile) was used, an amount of a specific binding of [$^{35}$S] GTPγS was increased in a concentration-dependent manner, by an addition of 5-oxo-ETE, 5-HPETE, arachidonic acid, eicosa-5Z,8Z,11Z-trienoic acid, 5-HETrE, eicosa-5Z,8Z-dienoic acid, 5-HETE and ETI.

When a membrane fraction containing a fusion protein of TG1019 protein and $G_{s\alpha L}$ was used, there was no observed increase in a specific binding amount, due to the addition of these compounds. On the contrary, when a membrane fraction containing a fusion protein of TG1019 protein and $G_{q\alpha}$ was used, a specific binding amount was increased by addition of 5-oxo-ETE and 5-HPETE, however, the amount increase was small, as compared to the case in which $G_{i\alpha}$ was used.

From the above results, it was expected that TG1019 protein is a G-protein coupled receptor, which couples with $G_{i\alpha1}$ or $G_{q\alpha}$. Further, it was found that 5-oxo-ETE, 5-HPETE, arachidonic acid, eicosa-5Z,8Z,11Z-trienoic acid, 5-HETrE, eicosa-5Z,8Z-dienoic acid, 5-HETE and ETI act as a ligand (an agonist).

In other words, the TG1019 protein was expected to be a G-protein coupled receptor having an eicosanoid, such as 5-oxo-ETE, 5-HPETE, arachidonic acid, eicosa-5Z,8Z,11Z-trienoic acid, 5-HETrE, eicosa-5Z,8Z-dienoic acid, 5-HETE and ETI as a ligand (an agonist).

Example 4

Identification of an Antagonist of TG1019 Protein (G-protein Coupled Receptor)

In the presence of 5-oxo-ETE (a ligand which acts as an agonist) and a test compound, a G-protein activating effect of TG1019 protein based on 5-oxo-ETE stimulation was detected, and an antagonistic effect of the test compound was examined.

Detection of the G-protein activation was carried out in a similar manner as in Example 3 (3) mentioned above, using a membrane fraction containing a fusion protein of TG1019 protein and $G_{i\alpha1}$ and a labeled GTPγS.

Specifically, a membrane fraction (450 µl) containing a fusion protein of TG1019 protein and $G_{i\alpha1}$ was suspended in a reaction solution (7.54 ml), and added thereto was 10 µl of GDP (10 mM). To 160 µl of this solution were added 5-oxo- ETE (the final concentration of 0.1 µM) and a test compound at various concentrations (0M, $10^{-7}$M - $10^{-5}$M), and the mixture was incubated at 30° C. for 10 minutes (a total amount of 5-oxo-ETE and the test compound: 20 µl).

Added thereto was 20 µl of [$^{35}$S] GTPγS to start a reaction. After incubation at 30° C. for one hour, the reaction was terminated by filtration through a glass filter.

An amount of the [$^{35}$S] GTPγS (a binding amount to the membrane fraction) on the filter was measured by liquid scintillation counting. From the thus measured [$^{35}$S] GTPγS amount was subtracted a nonspecific binding amount (a binding amount measured in the presence of 10 µM GTPγS), to obtain a specific binding amount.

As a result, it was found that various kinds of polyunsaturated fatty acid compounds inhibit the G-protein activating effect of TG1019 protein based on 5-oxo-ETE stimulation, showing an antagonistic effect.

The thus identified compound which acts as an antagonist of TG1019 protein (G-protein coupled receptor) and their $IC_{50}$ values are shown in Table 1 below.

TABLE 1

| Compound | $IC_{50}$ (µM) |
| --- | --- |
| DHA (4Z, 7Z, 10Z, 13Z, 16Z, 19Z-docosahexaenoic acid) | 1.6 ± 0.2 |
| EPA (5Z, 8Z, 11Z, 14Z, 17Z-eicosapentaenoic acid) | 6.0 ± 1.2 |
| Dihomo-γ-linolenic accid | 3.7 ± 0.7 |
| Eicosa-11Z, 14Z, 17Z-trienoic acid | 5.1 ± 0.6 |

Example 5

Confirmation of Expression and Function of TG1019 Protein (G-protein Coupled Receptor) in CHO Cells A TG1019 protein expression vector was transiently introduced to CHO cells to have a recombinant TG1019 protein expressed, and using these cells, a function of TG1019 protein as an eicosanoid receptor was confirmed.

At first, a DNA encoding an entire region of TG1019 protein obtained in Example 1 (1) mentioned above was subcloned in NotI recognition site of a vector plasmid pcDNA3.1 (an expression vector, available from Invitrogen), to obtain TG1019 protein expression vector plasmid pcDNA3.1-TG1019.

CHO cells ($1×10^6$ cells) were cultured in DMEM/F-12 culture medium supplemented with 10% fetal bovine serum at 37° C. for 20 hours. Using these cells, transfection was carried out by adding plasmid DNA (pcDNA3.1-TG1019, or as a control, vector pcDNA3.1) (5 µg) and transfection reagent (LipofectAMINE, available from Invitrogen), and the mixture was cultured for 24 hours. In case of using pretreatment with pertussis toxin, pertussis toxin (100 ng) was added after 20 hours of culture and the mixture was successively cultured for 4 hours.

The cells after culture were collected, washed, and suspended in a KRH buffer (Krebs-Ringer Hepes buffer, pH 7.4) containing rolipram (25 mM). The suspension was incubated at 37° C. for 30 minutes and inoculated in a 96 well plate ($5-7.5×10^4$ cells/90 µl/well).

Subsequently, KRH buffer (90 µl/well) containing forskolin (1 µM) and 5-oxo-ETE (the final concentration 0M or $10^{-11}$ to $10^{-5}$ M) was added thereto, and after the mixture was incubated at room temperature for 10 minutes, the cells were lysed to measure a cAMP production amount.

The cAMP production amount was measured using cAMP enzyme immunoassay system available from Amersham Biosciences.

As a result, in the cells to which only a vector was introduced, the cAMP production amount upon forskolin stimulation was not changed by addition of 5-oxo-ETE. On the other hand, in the cells in which pcDNA3.1-TG1019 was introduced and TG1019 protein was expressed, the cAMP production amount upon forskolin stimulation was inhibited by addition of 5-oxo-ETE, in a concentration-dependent manner.

Further, when the cells expressing TG1019 protein was pretreated with pertussis toxin, which inactivates sensitive G-proteins, cAMP production was not inhibited by addition of 5-oxo-ETE.

From these rsults, it can be confirmed that TG1019 protein is an eicosanoid receptor having 5-oxo-ETE as a ligand (a ligand which acts as an agonist), and it is a G-protein coupled receptor which couples with $G_i$ (adenylate cyclase inhibitory G-protein)

Example 6

Assay Using Cells Stably Expressing TG1019

(1) Preparation of cells stably expressing TG1019 Cells stably expressing TG1019 (the receptor protein of the present invention) and cells not expressing TG1019 were prepared by introducing to CHO cells the TG1019 protein expression vector prepared in Example 5 and the control vector, as described below.

First, CHO cells were inoculated onto a culture dish with a diameter of 6 cm to $1×10^6$ cells/dish, and incubated at 37° C. for 20 hours in a $CO_2$ incubator. For the culture medium, DMEM/F-12 medium supplemented with 10% fetal bovine serum was used. The supernatant was removed, and the culture dish was rinsed with a transfection medium (OPTI-MEM-I, available from Invitrogen) once, and 3 ml of cation-DNA solution was added. The cation-DNA solution was prepared as follows.

3 µg of pcDNA3.1-TG1019 (or a vector pcDNA3.1 without insertion) was diluted with a transfection medium to 300 µl, and added thereto was a solution of a transfection reagent (12 µl) (LipofectAMINE, available from Invitrogen) diluted with the transfection medium to 300 µl. The reaction proceeded at room temperature for 45 minutes. Subsequently, 2.4 ml of the transfection medium was added thereto, to prepare the cation-DNA solution.

The cells added with cation-DNA solution was cultured at 37° C. for 5 hours in a $CO_2$ incubator. Then, supernatant was removed, and 6 ml of DMEM /F12 culture medium supplemented with 10% fetal bovine serum was added thereto, and the cells were incubated at 37° C. for 24 hours in a $CO_2$ incubator. The cells were dissociated by trypsin-EDTA solution, and suspended in 10 ml of culture medium. This cell suspension (100 µl) was added to a culture dish with a diameter of 10 cm containing 10 ml of the culture medium, and was incubated at 37° C. for 24 hours in a $CO_2$ incubator. Subsequently, added thereto was hygromycin B with a final concentration of 800 µg/ml, and the mixture was cultured for 2 weeks in a $CO_2$ incubator. During that period, the medium containing hygromycic B was replaced every 3 to 4 days. Clones were generated by picking up colonies of the cells, and they were cultured in a medium containing hygromycin B.

The cells stably expressing TG1019 (or the cells not expressing TG1019) were obtained thereby.

(2) Measurement of Change in Intracellular Calcium Level by 5-oxo-ETE Stimulation The cells stably expressing TG1019 prepared in the above section (1) was incubated in DMEM/F12 medium supplemented with 10% fetal bovine serum at 37° C. in a $CO_2$ incubator. To the cells which were 80 to 90% confluent, was added a cell dissociation buffer (Cell Dissociation Buffer Enzyme-free PBS-based, available from Invitrogen), and cells were dissociated by incubating at 37° C. for 5 minutes. The cell suspension was suspended in 10 ml of DMEM/F12 medium supplemented by 10% fetal bovine serum, and the suspension was centrifuged (600×g, 4 minutes, 4° C.) to collect the cells. The collected cells were once centrifuged in an assay buffer [10 mM HEPES (pH 7.4), 140 mM NaCl, 5 mM KCl, 1 mM $CaCl_2$, 1 mM $MgCl_2$, 0.18% D-glucose], and the supernatant was removed. Then, the cells were suspended in 5 ml of a loading buffer (an assay buffer containing 3 μM FuraII-AM, [Dojindo Laboratories] and 0.05% Cremophor, [Nakarai tesque]) per a culture dish having a diameter of 10 cm, and loading was carried out at 37° C. for 60 minutes in a $CO_2$ incubator. During that period, the tube was overturned for mixing, every 15 minutes.

The cells after loading were centrifuged once with an assay buffer, to remove supernatant, and then, they were suspended in an assay buffer to have a concentration of 3.7 to $6.3 \times 10^6$ cells/ml. This cell suspension was portioned into a 96 well plate by 80 μl/well, and the plate was set in a fluorescence measuring device (FDSS6000, [Hamamatsu Photonics]), and the reaction was started by adding a solution containing 5-oxo-ETE or 5-HETE in a 5 fold concentration dissolved in an assay buffer, by 20 μl/well. The measurement was done by measuring fluorescence intensity at 510 nm, with excitation wavelength of 340 nm and 380 nm.

As a result, as shown in FIG. 6, it was confirmed that the cells stably expressing TG1019 showed an increase in intracellular calcium level by stimulation of 5-oxo-ETE and 5-HETE.

(3) Migration Test Using the Cells Stably Expressing TG1019

The cells stably expressing TG1019 and the cells not expressing the same obtained in the above section (1) were cultured in a medium (DMEM/F12 medium supplemented with 10% fetal bovine serum [GibcoBRL]), containing 800 μg/ml of hygromycin B. The cells which were 80 to 90% confluent were dissociated by a cell dissociation buffer, and the cells were washed twice by centrifugation (600×g, 5 minutes, 4° C.) with 10 ml of RPMI1640 culture medium supplemented with 0.1% BSA Then, the cells were prepared to a concentration of $1 \times 10^6$ cells/ml in the same medium.

Cell migration test was carried out using 2 chambers for migration test (Transwell; 8 μm pore, 24 well, 3422 [Costar]). Chambers were set in a plate, and a solution (600 μl) containing 5-oxo-ETE was added to the lower chamber, and the cell solution (100 μl) was added to the upper chamber, to start the reaction. Migration was carried out at 37° C. for 5 hours in a $CO_2$ incubator.

The chambers were removed, and 1.5 ml of the solution in the lower chamber was transferred to a tube, and centrifuged at 600×g, 3 minutes, 4° C. 300 μl of the supernatant was removed, and RPMI1640 culture medium supplemented with 0.1% BSA (not containing phenol red) was added, if needed, to adjust a volume of the cell solution to 300 μl. The number of the cells migrated to the lower chamber were counted by flow cytometer.

As a result, as shown in FIG. 7, the cells stably expressing TG1019 showed 5-oxo-ETE-induced migration, while the cells not expressing TG1019 did not. This results show that the cell migration is a phenomenon mediated by the TG1019 receptor.

(4) Assay for an Effect of an Antagonist (Change in Intracellular Calcium Level by Stimulation of 5-oxo-ETE and Migration Test Using Cells Stably Expressing TG1019)

Assays similar to those in the above sections (2) and (3) are carried out, except for adding (or not adding) a test compound (an antagonist) together with 5-oxo-ETE.

From these assays, effects of the test compounds (antagonists) are detected or confirmed.

Example 7

Migration Test Using Eosinophils and Neutrophils (1) Purification of Eosinophils Blood was collected (50 ml) from healthy male adult volunteers, and from the collected peripheral blood, eosinophils were purified as follows.

First, 12.5 ml each of the collected blood was poured into a 50 ml tube containing 23 ml physiological saline, and then, the total volume was adjusted to 40 ml with physiological saline. To a bottom of the tube, Percoll solution (specific gravity: 1.090±0.004, 10 ml) was gently added, and the mixture was centrifuged at 430×g, for 20 minutes at room temperature, without deceleration or acceleration. After removing a blood plasma fraction and a monocyte fraction, the remaining fraction was subjected to hemolysis. Hemolysis was performed as follows. 18 ml of cooled and purified water was added thereto and the mixture was stirred. 30 seconds later, 2 ml of 10×PIPES (1.10 M NaCl, 50 mM KCl, 250 mM PIPES (pH 7.4), 54 mM D-glucose) was added thereto and the mixture was stirred, and then, centrifuged at 430×g, for 6 minutes at 4° C.

After removing the supernatant, the cells were suspended by tapping, and hemolysis procedure was repeated once again. The cells were suspended in 40 ml of HBSS supplemented with 0.1% BSA containing [GibcoBRL], and centrifuged at 430×g, for 6 minutes at 4° C. The supernatant was removed and the cells were suspended in 10 ml of the same solution. Number of the cells were counted, and an existing ratio of eosinophils and neutrophils was measured (The number of the cells were counted by dyeing the same with trypan blue, using a hemocytometer. The measurement of the existing ratio was done by attaching the cells onto a glass slide, carrying out Diffquick dyeing, and observing the cells by a microscope). Thus, a fraction containing eosinophils and neutrophils in a high ratio was obtained.

Subsequently, from the above-obtained fraction, the netrophils were removed as follows.

First, the cell suspension was added to a 15 ml tube so that it contains $3 \times 10^7$ cells of neutrophils, and it was centrifuged at 430×g, for 6 minutes at 4° C. The supernatant was removed, and to the cell sediments was added 20 μl of 0.5 mg/ml human CD16 antibodies [Pharmingen]. Further added thereto was 800 μl of HBSS supplemented with 0.1% BSA, and the mixture was incubated on ice for 30 minutes. During this period, the tube was tapped every 10 minutes. Added thereto was 10 ml of HBSS supplemented with 0.1% BSA, and the mixture was centrifuged at 430×g, for 6 minutes at 4° C. The supernatant was removed, and the cells were suspended in 1 ml RPMI1640 culture medium supplemented with 10% fetal bovine serum. This cell suspension and 1 ml of dynabeads suspended in the above-mentioned media were mixed, and the mixture was incubated at 4° C. for 45 minutes, using a rotator. The dynabeads were prepared as follows. The dynabeads of [total cell number/(0.88×10⁸)]ml were washed twice with HBSS supplemented with 0.1% BSA, and washed once with RPMI1640 culture medium supplemented with 10% fetal bovine serum, and then suspended in 1 ml of RPMI1640 culture medium supplemented with 10% fetal bovine serum, in each tube. After the reaction, the dynabeads were removed using a magnet, and the collected cell solution was centrifuged at 430×g, for 6 minutes at 4° C. The supernatant was removed, and the resultant was suspended in 2 ml of RPMI1640 culture medium supplemented with 10% fetal bovine serum. As a result of measurements of number of cells and an eosinophil existing ratio, carried out in a similar manner as above, eosinophil existing ratio was 93%.

(2) Purification of Neutrophils

Neutrophils were purified as follows. Blood was collected (50 ml) from healthy male adult volunteers. Then, 12.5 ml each of the collected blood was poured into a 50 ml tube containing 23 ml physiological saline, and, the total volume was adjusted to 40 ml with physiological saline. To a bottom of the tube, Percoll solution (specific gravity: 1.079±0.004, 10 ml) was gently added, and the mixture was centrifuged at 430×g, for 20 minutes at room temperature, without deceleration or acceleration.

After removing a blood plasma fraction and a monocyte fraction, the remaining fraction was subjected to hemolysis twice in a similar manner as in the above section (1). The cells after hemolysis were suspended in 50 ml of RPMI1640 culture medium supplemented with 10% fetal bovine serum, and the suspension was centrifuged at 430×g, for 5 minutes at 4° C. The supernatant was removed, and the resultant was suspended in 10 ml of the same culture medium. Number of cells and a neutrophil existing ratio were measured in a similar manner as in the section (1). The neutrophil existing ratio was 97%.

(3) Migration Test of Eosinophils and Neutrophils

After washing the eosinophils and neutrophils purified in the above sections, the cells were suspended in RPMI1640 supplemented with 0.1% BSA (not containing phenol red) which contains 3 µM Calcein-AM (Dojindo laboratories, fluorescence reagent), so that the cell count became 1×10⁶ cells/ml. The suspension was incubated at 37° C. for 30 minutes. The cells were washed twice with the same culture medium, and suspended in the same medium so that the cell count became 1×10⁶ cells/ml.

Using these cells, cell migration test was carried out using 2 chambers for migration test (Transwell; 3 µm pore, 24 well, 3422 [Costar]). Chambers were set in a plate, and for the eosinophil cell solution, an eicosanoid solution containing 5-oxo-ETE, LTB4 or 5-HETE was added to the lower chamber in amount of 600 µl each, and for the neutrophil cell solution, an eicosanoid solution containing 5-oxo-ETE or LTB4 was added to the lower chamber in amount of 600 µl each. The cell solution of eosinophils or neutrophils (100 µl) was added to the upper chamber, to start the reaction. Migration was carried out at 37° C. in a $CO_2$ incubator, for 1.5 hours for the eosinophils, and for 2 hours for the neutrophils.

After the reaction, the chambers were removed, and to the lower chamber was added 66 µl of 10× lysis buffer (5% Triton X-100 dissolved in PBS, 10% ethanol). Cell lysate was prepared by shaking the mixture for 10 minutes under light-shielded condition at room temperature. 200 µl of the cell lysate was transferred to 96 well black plate (237105, Nunc), and fluorescence intensities were measured using a fluorometer (ARVO™ SX, Wallac) with an excitation wavelength of 485 nm and a fluorescence wavelength of 535 nm.

As a result, as shown in FIG. 8A (eosinophil) and FIG. 8B (neutrophil), it was shown that 5-oxo-ETE has an ability to make these cells migrate.

(4) Assay for an Effect of an Antagonist (Migration Test of Eosinophils and Neutrophils)

Assays similar to that in the above section (3) are carried out, except for adding (or not adding) a test compound (an antagonist) together with 5-oxo-ETE to the upper chamber of the 2 chambers, to examine migrations of the eosinophils and neutrophils. It can be confirmed that cell migrations are inhibited in the presence of the antagonist.

Example 8

Apoptosis Analysis

PC3 human prostate cancer cells, which had been cultured in RPMI1640 culture medium supplemented with 10% fetal bovine serum were dissociated by trypsin-EDTA solution (GibcoBRL), and suspended in RPMI1640 culture medium supplemented with 0.5% fetal bovine serum. The cells were plated onto a 6 cm Petri dish to 2×10⁵ cells/dish, and cultured at 37° C. for 18 hours in a $CO_2$ incubator. The supernatant was removed and 1980 µl of the same medium was added, and 20 µl of 1 mM DHA was further added thereto, and the mixture was cultured at 37° C. for 2 hours in a $CO_2$ incubator.

In addition, as a test in the presence of 5-oxo-ETE, 1960 µl of RPMI1640 culture medium supplemented with 0.5% fetal bovine serum was added, and 20 µl of a 100 µM 5-oxo-ETE solution and 20 µl of a 1 mM DHA solution were further added thereto, and the cells were cultured in a similar manner as described above.

The adhered cells were removed by a cell scraper, transferred to a 1.5 ml tube, and centrifuged at 800×g for 5 minutes at 4° C., to collect suspended and adhered cells. The cells were washed twice by centrifugation with 1 ml of PBS(−), and dyed with annexin, using a kit for detecting apoptosis (TACS™ Annexin V Kits [Trevigen]). The cells were suspended in 100 µl of a FITC-Annexin solution, and after 15 minutes of reaction under light-shielded condition at room temperature, 300 µl of Binding buffer was added thereto, and the FITC-Annexin bound to the cells and propidium iodide (PI) uptake into the cells were measured, by means of flow cytometer [Becton Dickinson].

As shown in FIG. 9, it was shown that number of cells showing positive annexin dyeing and negative PI uptake (which means the cells at an early stage of apoptosis) increased, and thereby it was concluded that DHA induces apoptosis of PC3 cells. Further, it was also shown that the induction of apoptosis was inhibited by 5-oxo-ETE.

Reference Example 1

Analysis of TG1019 Expression in Eosinophils and PC3 Prostate Cancer Cells (mRNA Expression Analysis by RT-PCR)

(1) RNA Extraction and cDNA Synthesis

Extraction of total RNA from eosinophils was carried out as follows. The purified eosinophils (1×10⁶ cells) were washed twice with PBS by centrifugation at 400×g for 6 minutes at 4° C. The cells were suspended in 1 ml of an RNA extraction reagent (ISOGEN [NIPPON GENE]), and left alone at room temperature for 5 minutes. Subsequently, 200 µl of chloroform was added thereto, and the mixture was vigorously stirred for 15 seconds, then left alone at room temperature for 3 minutes. The mixture was centrifuged at 12,000×g for 15 minutes at 4° C., and an aqueous phase was transferred to another tube. Added thereto was 500 μl of isopropanol, and the mixture was stirred and left alone at room temperature for 10 minutes, and centrifuged at 12,000×g for 10 minutes at 4° C. The supernatant was removed, and 1 ml of 70% ethanol was added thereto and the mixture was vigorously stirred, and centrifuged at 7,500×g for 5 minutes at 4° C. After removing the supernatant, the sediments were dissolved in 500 μl of sterilized and purified water, to give a total RNA solution.

Extraction of total RNA from PC3 cells was carried out as follows. The PC3 cells cultured in RPMI1640 culture medium supplemented with 10% fetal bovine serum for 2 days at 37° C. in a $CO_2$ incubator. The cells were rinsed twice with PBS, and extraction of total RNA was carried out according to a protocol provided for Rneasy Mini Kit (Qiagen).

Using the above prepraed RNAs, cDNAs were obtained by reverse transcription as follows.

0.2 μg of total RNA, 0.5 μg of oligo (dT) 12-18 primer [Invitrogen], 1 μl of 10 mM dNTP solution were mixed, and the total volume was adjusted to 12 μl by sterilized water. The mixture was incubated at 65° C. for 5 minutes by a thermal cycler, (GeneAmp PCR System 9700:PE Applied Biosystem), and then left alone on ice for one minute. To the above solution were added 4 μl of 5× buffer, 2 μl of 0.1 M DTT solution, and 1 μl of sterilized water, and the mixture was incubated at 42° C. for 2 minutes using a thermal cycler. Then, 1 μl of 200U/μl reverse transcriptase (SuperScript™ II Reverse Transcriptase [Invitrogen]) was added thereto, and the mixture was incubated at 42° C. for 50 minutes, subsequently at 70° C. for 15 minutes to prepare a cDNA solution.

(2) Analysis on Expression of mRNA by PCR

Using the above-obtained cDNA, PCR reaction was carried out as follows. 2 μl of a cDNA solution, 4 μl of 10× buffer [Clontech], 3.2 μl of 2.5 mM dNTP solution [Takara Bio], 0.6 μl of Advantage 2 polymerase Mix [Clontech], 1 μl each of 10 μM sense and antisense primers, and 26.2 μl of sterilized water were mixed in a tube, and PCR reaction was carried out, using a thermal cycler, under condition of 95° C.-1 minute, (95° C.-30 seconds, 68° C.-1.5 minutes)×30 cycles, and 68° C.-2 minutes. The sample after reaction was subjected to agarose gel electrophoresis (1% L03 [Takara Bio]), to confirm a band. As a primer for confirming mRNA expression of 5-oxo-ETE receptor, the following synthetic oligonucleotide was used. Sense Primer: 5'-TCCCTCTGCCTTTACCACT-GTGGG-3' (SEQ ID NO:22), Antisense Primer: 5'-GTAG-GAGCTCTCGTCGCTCACTG-3' (SEQ ID NO:23) (As a primer for confirming mRNA expression of G3PDH for control, Human Glyceraldehyde 3-phosphate Dehydrogenase Control Amplifier Set [Clontech]) was used.

As a result, in both eosinophils and PC3 cells, expressions of mRNA of TG1019 were confirmed. Further, it was also confirmed that the generated band was not genome-derived one, since there was no band observed in a sample used as a control in which reverse transcription was not carried out.

INDUSTRIAL APPLICABILITY

The receptor protein (TG1019) of the present invention and the gene thereof are useful for research on a mechanism of intracellular signal transduction. Further, the receptor protein (TG1019) of the present invention can be a new target molecule for a therapeutic agent for a new disease.

In addition, the method for screening, identifying, and characterizing an effector (an agonist or an antagonist), using the receptor protein of the present invention and the gene thereof is useful for research and development of a new pharmaceutical.

Further, the pharmaceutical composition comprising as an effective ingredient an antagonist of the receptor protein of the present invention, and the therapeutic method comprising administering an effective amount of the antagonist to a patient is useful for treatment of immunological diseases in which migrations of eosinophils or neutrophils are involved in onset of the pathological state, or for treatment of cancer.

The invention claimed is:

1. A method for screening or identifying an antagonist of an eicosanoid receptor protein, comprising:
   (1) bringing the receptor protein into contact with a test compound and a ligand;
   (2) detecting the function or the activity of the receptor protein; and
   (3) determining whether or not the test compound has an ability to inhibit the function or the activity of the receptor protein, or determining an intensity of the ability:
wherein the function or the activity of the receptor protein is selected from the following (i), (ii) and (iii),
   (i) specific binding to a ligand,
   (ii) induction of intracellular signal transductions based on a stimulation by a ligand, and
   (iii) activation of G-protein based on a stimulation by a ligand;
where the ligand is an eicosanoid; and said receptor protein is a polypeptide selected from (A) and (B);
   (A) a polypeptide comprising an amino acid sequence shown by SEQ ID NO:2 or SEQ ID NO:21; and
   (B) a polypeptide encoded by a nucleic acid which hybridizes under highly stringent condition with a nucleic acid comprising a nucleotide sequence shown by SEQ ID NO:1 or SEQ ID NO:20 and having a function or activity as a receptor of an eicosanoid;
said hybridization under highly stringent condition being carried out by conducting hybridization for 16 hours at a temperature of 50 to 60° C. in 6×SSC or in a hybridization solution having an equivalent salt concentration to 6×SSC, followed by preliminary washing with 6×SSC or with a solution having an equivalent salt concentration to 6×SSC, and subsequently followed by washing in 0.1×SSC or in a solution having an equivalent salt concentration to 0.1 SSC; and
said receptor protein is in a form of a cell over-expressing the receptor protein by introducing an exogenous nucleic acid encoding the receptor protein or by introducing an exogenous expression vector comprising the same.

2. The method according to claim 1, wherein the eicosanoid is selected from the group consisting of 5-oxo-ETE, 5-HPETE, arachidonic acid, eicosa-5Z,8Z,11Z-trienoic acid, 5-HETrE, eicosa-5Z,8Z-dienoic acid, 5-HETE and ETI.

3. The method according to claim 1, wherein the eicosanoid is 5-oxo-ETE.

4. The method according to claim 1, wherein the intracellular signal transduction is selected from change in $Ca^{2+}$ level, change in cAMP level, activation of phospholipase C, change in pH and change in $K^+$ level.

5. The method according to claim 1, wherein the activation of G-protein is an activation of an α subunit of a G-protein belonging to Gi subfamily.

6. The method according to any one of claim 1, for use in selection, identification or characterization of a pharmaceutical.

7. The method according to any one of claim 1, wherein the receptor protein is a polypeptide comprising an amino acid sequence shown by SEQ ID NO:2 or SEQ ID NO:21.

* * * * *